(12) United States Patent
Brustad et al.

(10) Patent No.: US 7,878,974 B2
(45) Date of Patent: Feb. 1, 2011

(54) HAND ACCESS LAPAROSCOPIC DEVICE

(75) Inventors: John R Brustad, Dana Point, CA (US);
Jeremy J Albrecht, Rancho Santa Margarita, CA (US); Nabil Hilal, Laguna Niguel, CA (US); Gary M Johnson, Mission Viejo, CA (US); Charles C Hart, Summerville, SC (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 12/815,986

(22) Filed: Jun. 15, 2010

(65) Prior Publication Data

US 2010/0249527 A1 Sep. 30, 2010

Related U.S. Application Data

(63) Continuation of application No. 11/548,955, filed on Oct. 12, 2006, now Pat. No. 7,736,306.

(60) Provisional application No. 60/726,826, filed on Oct. 14, 2006, provisional application No. 60/745,730, filed on Apr. 26, 2006, provisional application No. 60/803,346, filed on May 26, 2006, provisional application No. 60/803,965, filed on Jun. 5, 2006, provisional application No. 60/828,089, filed on Oct. 4, 2006.

(51) Int. Cl.
*A61B 1/32* (2006.01)

(52) U.S. Cl. .................................. 600/208; 600/233

(58) Field of Classification Search ............ 606/108, 606/206, 208; 600/201–246
See application file for complete search history.

(56) References Cited

U.S. PATENT DOCUMENTS

| 558,364 A | 4/1896 | Doolittle |
| 1,810,466 A | 6/1931 | Deutsch |
| 2,305,289 A | 12/1942 | Coburg |
| 2,478,586 A | 8/1949 | Krapp |

(Continued)

FOREIGN PATENT DOCUMENTS

EP 1 125 552 8/2001

(Continued)

OTHER PUBLICATIONS

Neil Sheehan, Supplemental Expert Report of Neil Sheehan, Re: U S Patent No. 5,741,298, United States District Court for the Central District of California, Civil Action No. SACV 03-1322 JVS, Aug. 9, 2005.

(Continued)

*Primary Examiner*—Eduardo C Robert
*Assistant Examiner*—Christina Negrelli
(74) *Attorney, Agent, or Firm*—Pui Tong Ho

(57) ABSTRACT

The invention relates to a hand access laparoscopy device having a gelcap, a retainer, a sleeve and a retention ring. The gelcap includes gel that is bonded to a cap. The cap includes an inner cylindrical wall to which the gel in bonded, thereby providing a sealing area between the device and the wound in a body wall. By securing the gel to the inner cylindrical wall, the thickness of the gel and corresponding cap is minimized along with the overall footprint of the device. With the gel thickness reduced and able to be substantially flush, the "doming" phenomenon produced by insufflation of a patient's abdomen is reduced.

17 Claims, 16 Drawing Sheets

U.S. PATENT DOCUMENTS

| | | |
|---|---|---|
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,111,943 A | 11/1963 | Orndorff |
| 3,195,934 A | 7/1965 | Parrish |
| 3,244,169 A | 4/1966 | Baxter |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,523,534 A | 8/1970 | Nolan |
| 3,717,151 A | 2/1973 | Collett |
| 3,831,583 A | 8/1974 | Edmunds, Jr. et al. |
| 3,841,332 A | 10/1974 | Treacle |
| 3,850,172 A | 11/1974 | Cazalis |
| 3,856,021 A | 12/1974 | McIntosh |
| 3,860,274 A | 1/1975 | Ledstrom et al. |
| 4,024,872 A | 5/1977 | Muldoon |
| 4,043,328 A | 8/1977 | Cawood, Jr. et al. |
| 4,069,913 A | 1/1978 | Harrigan |
| 4,083,370 A | 4/1978 | Taylor |
| 4,188,945 A | 2/1980 | Wenander |
| 4,217,664 A | 8/1980 | Faso |
| 4,222,126 A | 9/1980 | Boretos et al. |
| 4,254,973 A | 3/1981 | Benjamin |
| 4,338,937 A | 7/1982 | Lerman |
| 4,367,728 A | 1/1983 | Mutke |
| 4,454,873 A | 6/1984 | Laufenberg et al. |
| 4,475,548 A | 10/1984 | Muto |
| 4,550,713 A | 11/1985 | Hyman |
| 4,553,537 A | 11/1985 | Rosenberg |
| 4,691,942 A | 9/1987 | Ford |
| 4,755,170 A | 7/1988 | Golden |
| 4,777,943 A | 10/1988 | Chvapil |
| 4,798,594 A | 1/1989 | Hillstead |
| 4,802,694 A | 2/1989 | Vargo |
| 4,842,931 A | 6/1989 | Zook |
| 4,856,502 A | 8/1989 | Ersfeld et al. |
| 4,863,438 A | 9/1989 | Gauderer et al. |
| 4,889,107 A | 12/1989 | Kaufman |
| 4,895,565 A | 1/1990 | Hillstead |
| 4,903,710 A | 2/1990 | Jessamine et al. |
| 4,911,974 A | 3/1990 | Shimizu et al. |
| 4,926,882 A | 5/1990 | Lawrence |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,009,224 A | 4/1991 | Cole |
| 5,015,228 A | 5/1991 | Columbus et al. |
| 5,037,379 A | 8/1991 | Clayman et al. |
| 5,082,005 A | 1/1992 | Kaldany |
| 5,178,162 A | 1/1993 | Bose |
| 5,192,301 A | 3/1993 | Kamiya et al. |
| 5,207,656 A | 5/1993 | Kranys |
| 5,213,114 A | 5/1993 | Bailey, Jr. |
| 5,299,582 A | 4/1994 | Potts |
| 5,316,541 A | 5/1994 | Fischer |
| 5,350,364 A | 9/1994 | Stephens et al. |
| 5,353,786 A | 10/1994 | Wilk |
| 5,366,478 A | 11/1994 | Brinkerhoff et al. |
| 5,368,545 A | 11/1994 | Schaller et al. |
| 5,380,288 A | 1/1995 | Hart et al. |
| 5,389,080 A | 2/1995 | Yoon |
| 5,389,081 A | 2/1995 | Castro |
| 5,407,433 A | 4/1995 | Loomas |
| 5,429,609 A | 7/1995 | Yoon |
| 5,435,943 A | 7/1995 | Adams et al. |
| 5,437,683 A | 8/1995 | Neumann et al. |
| 5,441,486 A | 8/1995 | Yoon |
| 5,460,616 A | 10/1995 | Weinstein et al. |
| 5,476,475 A | 12/1995 | Gadberry |
| 5,480,410 A | 1/1996 | Cuschieri et al. |
| 5,486,426 A | 1/1996 | McGee et al. |
| 5,492,304 A | 2/1996 | Smith et al. |
| 5,496,280 A | 3/1996 | Vandenbroek et al. |
| 5,503,112 A | 4/1996 | Luhman et al. |
| 5,514,133 A | 5/1996 | Golub et al. |
| 5,518,278 A | 5/1996 | Sampson |
| 5,522,791 A | 6/1996 | Leyva |
| 5,524,644 A | 6/1996 | Crook |
| 5,531,758 A | 7/1996 | Uschold et al. |
| 5,545,179 A | 8/1996 | Williamson, IV |
| 5,562,677 A | 10/1996 | Hildwein et al. |
| 5,603,702 A | 2/1997 | Smith et al. |
| 5,628,732 A | 5/1997 | Antoon, Jr. et al. |
| 5,632,284 A | 5/1997 | Graether |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,672,168 A | 9/1997 | de la Torre et al. |
| 5,681,341 A | 10/1997 | Lunsford et al. |
| 5,709,664 A | 1/1998 | Vandenbroek et al. |
| 5,720,730 A | 2/1998 | Blake, III |
| 5,728,103 A | 3/1998 | Picha et al. |
| 5,741,298 A | 4/1998 | MacLeod |
| 5,753,150 A | 5/1998 | Martin et al. |
| 5,782,817 A | 7/1998 | Franzel et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,810,721 A | 9/1998 | Mueller et al. |
| 5,813,409 A | 9/1998 | Leahy et al. |
| 5,814,026 A | 9/1998 | Yoon |
| 5,832,925 A | 11/1998 | Rothrum |
| 5,841,298 A | 11/1998 | Huang |
| 5,853,395 A | 12/1998 | Crook et al. |
| 5,865,729 A | 2/1999 | Meehan et al. |
| 5,865,807 A | 2/1999 | Blake, III |
| 5,895,377 A | 4/1999 | Smith et al. |
| 5,899,208 A | 5/1999 | Bonadio |
| 5,904,703 A | 5/1999 | Gilson |
| 5,906,577 A | 5/1999 | Beane et al. |
| 5,919,476 A | 7/1999 | Fischer et al. |
| 5,947,922 A | 9/1999 | MacLeod |
| 5,951,588 A | 9/1999 | Moenning |
| 5,964,781 A | 10/1999 | Mollenauer et al. |
| 5,980,806 A | 11/1999 | Ohmi et al. |
| 5,989,233 A | 11/1999 | Yoon |
| 5,993,471 A | 11/1999 | Riza et al. |
| 5,993,485 A | 11/1999 | Beckers |
| 5,997,515 A | 12/1999 | de la Torre et al. |
| 6,010,494 A | 1/2000 | Schafer et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,045,535 A | 4/2000 | Ben Nun |
| 6,093,358 A | 7/2000 | Schiewe et al. |
| 6,142,936 A | 11/2000 | Beane et al. |
| 6,149,642 A | 11/2000 | Gerhart et al. |
| 6,162,172 A | 12/2000 | Cosgrove et al. |
| 6,254,533 B1 | 7/2001 | Fadem et al. |
| 6,254,534 B1 | 7/2001 | Butler et al. |

| | | |
|---|---|---|
| 6,325,384 B1 | 12/2001 | Berry, Sr. et al. |
| 6,375,877 B2 | 4/2002 | Lauf et al. |
| 6,382,211 B1 | 5/2002 | Crook |
| 6,383,162 B1 | 5/2002 | Sugarbaker |
| 6,406,499 B1 | 6/2002 | Kania |
| 6,413,244 B1 | 7/2002 | Bestetti et al. |
| 6,413,458 B1 | 7/2002 | Pearce |
| 6,440,063 B1 | 8/2002 | Beane et al. |
| 6,450,983 B1 | 9/2002 | Rambo |
| 6,482,181 B1 | 11/2002 | Racenet et al. |
| 6,485,435 B1 | 11/2002 | Bakal |
| 6,533,734 B1 | 3/2003 | Corley, III et al. |
| 6,551,344 B2 | 4/2003 | Thill |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,613,952 B2 | 9/2003 | Rambo |
| 6,623,426 B2 | 9/2003 | Bonadio et al. |
| 6,702,787 B2 | 3/2004 | Racenet et al. |
| 6,723,044 B2 | 4/2004 | Pulford et al. |
| 6,814,078 B2 | 11/2004 | Crook |
| 6,846,287 B2 | 1/2005 | Bonadio et al. |
| 6,866,861 B1 | 3/2005 | Luhman |
| 6,895,965 B2 | 5/2005 | Scarberry et al. |
| 6,902,541 B2 | 6/2005 | McNally et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,997,909 B2 | 2/2006 | Goldberg |
| 7,033,319 B2 | 4/2006 | Pulford et al. |
| 7,052,454 B2 | 5/2006 | Taylor |
| 7,081,089 B2 | 7/2006 | Bonadio et al. |
| 2001/0037053 A1 | 11/2001 | Bonadio et al. |
| 2002/0002324 A1 | 1/2002 | McManus |
| 2002/0010388 A1 | 1/2002 | Taylor et al. |
| 2002/0038077 A1 | 3/2002 | de la Torre et al. |
| 2002/0072762 A1 | 6/2002 | Bonadio et al. |
| 2003/0040711 A1 | 2/2003 | Racenet et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael et al. |
| 2004/0015185 A1 | 1/2004 | Ewers et al. |
| 2004/0049100 A1 | 3/2004 | Butler et al. |
| 2004/0073090 A1 | 4/2004 | Butler et al. |
| 2004/0092796 A1 | 5/2004 | Butler et al. |
| 2004/0106942 A1 | 6/2004 | Taylor et al. |
| 2004/0127772 A1 | 7/2004 | Ewers et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0254426 A1 | 12/2004 | Wenchell |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0090717 A1 | 4/2005 | Bonadio et al. |
| 2005/0148823 A1 | 7/2005 | Vaugh et al. |
| 2005/0155611 A1 | 7/2005 | Vaugh et al. |
| 2005/0197537 A1 | 9/2005 | Bonadio et al. |
| 2005/0222582 A1 | 10/2005 | Wenchell |
| 2005/0241647 A1 | 11/2005 | Nguyen et al. |
| 2005/0267419 A1 | 12/2005 | Smith |
| 2005/0283050 A1 | 12/2005 | Gundlapalli et al. |
| 2005/0288558 A1 | 12/2005 | Ewers et al. |
| 2006/0030755 A1 | 2/2006 | Ewers et al. |
| 2006/0047284 A1 | 3/2006 | Gresham |
| 2006/0052669 A1 | 3/2006 | Hart |
| 2006/0084842 A1 | 4/2006 | Hart et al. |
| 2006/0129165 A1 | 6/2006 | Edoga et al. |
| 2006/0149306 A1 | 7/2006 | Hart et al. |
| 2006/0161050 A1 | 7/2006 | Butler et al. |

FOREIGN PATENT DOCUMENTS

| | | |
|---|---|---|
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S960196 | 8/1997 |
| IE | S970810 | 11/1997 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 11-290327 | 10/1999 |
| JP | 2002-28163 | 1/2002 |
| JP | 02003 235879 A | 8/2003 |
| WO | WO95/07056 | 3/1995 |
| WO | WO95/22289 | 8/1995 |
| WO | WO 95/24864 | 9/1995 |
| WO | WO 95/27468 | 10/1995 |
| WO | WO 99/25268 | 5/1999 |
| WO | WO00/32116 | 6/2000 |
| WO | WO00/54675 | 9/2000 |
| WO | WO00/54676 | 9/2000 |
| WO | WO00/54677 | 9/2000 |
| WO | WO01/08581 | 2/2001 |
| WO | WO02/34108 | 5/2002 |
| WO | WO03/032819 | 4/2003 |
| WO | WO03/034908 | 5/2003 |
| WO | WO03/061480 | 7/2003 |
| WO | WO 2004/075730 | 9/2004 |
| WO | WO 2004/075741 | 9/2004 |
| WO | WO 2004/075930 | 9/2004 |
| WO | WO 2005/034766 | 4/2005 |

OTHER PUBLICATIONS

Dexterity Protractor Instruction Manual by Dexterity Surgical, Inc.
Horigane, et al , Technical Note: Development of a Duodoenal Cannula for Sheep, Journal of Animal Science, Apr. 1992, vol. 70, Issue 4, pp. 1216-1219.
Horigane, et al , Silicone Rumen Cannula with a Soft Cylindrical Part and a Hard Flange, Journal of Dairy Science, Nov. 1989 vol. 72, No. 11, pp. 3230-3232.
McSweeney, Cannullation of the Rumen in Cattle and Buffaloes, Australian Veterinary Journal, Aug. 1989, vol. 66, No. 8, pp. 266-268.
Yamazaki et al , Diurnal Changes in the Composition of Abomasal Digesta in Fasted and Fed Sheep, The Tohoku Journal of Argircultural Research, Mar. 1987, vol. 37, No. 3-4, pp. 49-58.
European Patent Office; International Search Report and The Written Opinion of the International Searching Authority for International Application No. PCT/US2006/040154, maile.
European Patent Office, International Search Report and The Written Opinion of the International Searching Authority for PCT Application No. PCT/US2006/039800 mailed Apr. 16.
Co-Pending U.S. Appl. No. 10/381,220, filed Mar. 20, 2003; Title: Surgical Access Apparatus and Method.
Co-Pending U.S. Appl. No. 10/516,198, filed Nov. 30, 2004; Title: Wound Retractor.
Co-Pending U.S. Appl. No. 10/927,551, filed Aug. 25, 2004; Title: Surgical Access System.
Co-Pending U.S. Appl. No. 11/244,647, filed Oct. 5, 2005; Title: Surgical Access Apparatus and Method.
Co-Pending U.S. Appl. No. 11/245,709, filed Oct. 7, 2005; Title: Surgical Access System.
Co-Pending U.S. Appl. No. 11/330,661, filed Jan. 12, 2006; Title: Sealed Surgical Access Device.

Co-Pending U.S. Appl. No. 11/548,746, filed Oct. 12, 2006; Title: Method of Making a Hand Access Laparoscopic Device.

Co-Pending U.S. Appl. No. 11/548,758, filed Oct. 12, 2006; Title: Split Hoop Wound Retractor With Gel Pad.

Co-Pending U.S. Appl. No. 11/548,765, filed Oct. 12, 2006; Title: Split Hoop Wound Retractor.

Co-Pending U.S. Appl. No. 11/548,767, filed Oct. 12, 2006; Title: Circular Surgical Retractor.

Co-Pending U.S. Appl. No. 11/548,781, filed Oct. 12, 2006; Title: Wound Retractor With Gel Cap.

Co-Pending U.S. Appl. No. 11/755,305, filed May 30, 2007; Title: Wound Retraction Apparatus and Method.

Co-Pending U.S. Appl. No. 11/564,409, filed Nov. 29, 2006; Title: Surgical Instrument Access Device.

The International Bureau of WIPO, International Preliminary Report on Patentability for International Application No. PCT/US2006/039800 dated Apr. 16, 2008.

Declaration of John R. Brustad Under 37 C.F. R. 1 132, dated Dec. 10, 2009.

"Applied GelPort™ Advanced Access Device" product sales brochure dated 2001.

"Cap Ring" production drawing dated Jan. 19, 2001.

"Gelport® Laparoscopic Hand Access System" product sales brochure dated 2005.

"Cap Ring Medium" production drawing dated Aug. 16, 2005.

HAND ACCESS LAPAROSCOPIC DEVICE

CROSS REFERENCE TO RELATED APPLICATIONS

This application is a divisional of U.S. application Ser. No. 11/548,955, filed Oct. 12, 2006, now U.S. Pat. No. 7,736,306, which claims the benefit of U.S. application Ser. No. 60/726,826, filed Oct. 14, 2005, of which the entire disclosures are incorporated by reference herein.

BACKGROUND OF THE INVENTION

This invention relates substantially to devices and other apparatuses facilitating sealed access with surgical instruments, such as a surgeon's hand, across a body wall and into a body cavity.

In several areas of surgery there exists a need to have mechanisms or devices that can seal a body cavity or space, and yet permit the introduction of surgical instruments such as guidewires, endoscopes, and even the hand of a surgeon. Typical of these areas of surgery is laparoscopic surgery that relies on surgical instruments inserted through the abdominal wall to reach an operative site within the abdominal cavity. In order to increase space around the operative site within the cavity, insufflation gases are typically introduced to inflate the cavity and elevate the abdominal wall. This pressurizing of the abdominal cavity is referred to as pneumoperitoneum. In this context, the need to seal the body cavity or space arises from the need to maintain the pneumoperitoneum even when instruments are present.

Trocars have been commonly used to provide instrument access in laparoscopic surgeries. These trocars have included elaborate seal structures having zero seals that prevent escape of the gases in the absence of instruments, and instrument seals that prevent escape of the gases in the presence of instruments. Unfortunately, the instrument seals have been able to accommodate only a narrow range of instrument diameters. Multiple seal pairs had to be provided where wider ranges were desired.

Some instruments, such as the hand of the surgeon, have been too large for trocar access. Under these circumstances, hand-assisted laparoscopic seals have been provided. Such devices have been large, cumbersome, and largely ineffective in providing the required sealing mechanism. Other access devices, such as Touhy-Borst seals, have been used, but only for very small diameter access such as that required by a guidewire.

Each of the prior devices suffers from drawbacks that make the device difficult or cumbersome to use. For example, a Touhy-Borst seal requires two hands to use and does not form a seal when a guidewire or other device is about to be introduced. Present trocar seals and hand-assisted seals require two valves, one forming an instrument seal in the presence of the instrument, and the other forming a zero seal in the absence of the instrument. For example, in hand-assisted devices, elaborate mechanisms have been required to seal around the surgeon's arm. When the arm is removed, a separate zero seal has been required to prevent the escape of blood or insufflation gases.

SUMMARY

The invention is directed to a surgical access device that is adapted for disposition relative to an incision in a body wall. The access device facilitates insertion of an instrument therethrough as well as maintenance of a sealing relationship with the instrument. The surgical access device includes a cap that is substantially annular and has an opening therethrough. The surgical access device also includes a gel pad that is coupled to the cap and adapted for insertion of the instrument therethrough. The gel pad covers and seals the entire opening of the cap. The surgical access device further includes a retainer that is substantially annular and adapted for placement against the body wall. Additionally, the surgical access device includes coupling means that are adapted for coupling the cap and the retainer together. The retainer is configured to be coupled to a proximal portion of an elongate sleeve that is adapted to extend through the incision. The retainer is also adapted, together with the elongate sleeve, to retract the incision.

In one aspect, the cap includes at least one gap along the annular perimeter of the cap. The at least one gap creates at least one first end and at least one second end of the cap. The at least one gap facilitates a transition in the cap from a first, larger periphery to a second, smaller periphery. In another aspect, the surgical access device also includes means for maintaining the periphery of the cap at the second, smaller periphery. In another aspect, when the cap is at the first, larger periphery, the retainer may be inserted into or removed from the opening of the cap, and the retainer may be fixedly coupled to the cap by first, transitioning the perimeter of the cap to the second, smaller periphery with the retainer positioned within the opening of the cap, and second, maintaining the periphery of the cap at the second, smaller periphery with the maintaining means. In one aspect, the maintaining means includes a squeeze release buckle fitting configured to couple the at least one first end of the cap to the at least one second end of the cap. The squeeze release buckle fitting includes a first, barbed portion that extends from the at least one first end of the cap and a second, receiver portion that extends from the at least one second end of the cap. The barbed portion and the receiver portion of the squeeze release buckle fitting are configured to engage each other in a mating relationship. In another aspect, the barbed portion of the squeeze release buckle fitting includes a plurality of arms, two of which are resilient and have projections extending therefrom. The receiver portion of the squeeze release buckle fitting has corresponding sidewalls for engaging the projections of the barbed portion, thereby causing the two arms that have the projections to flex toward each other as the arms slide into a channel defined by the receiver and to flex away from each other as the projections clear the ends of the sidewalls and into a fully engaged state. In another aspect, the cap includes at least a first gap and a second gap. The first and second gaps create first and second arc portions of the annular cap, each of which includes first and second ends. The first end of the first arc portion corresponds with the second end of the second arc portion and the second end of the first arc portion corresponds with the first end of the second arc portion. The first end of each of the first and second arc portions has a barbed portion of the squeeze release buckle fitting extending therefrom and the second end of each of the first and second arc portions has a corresponding receiver portion of the squeeze release buckle fitting extending therefrom. In another aspect, the maintaining means includes a latch that is pivotally coupled proximate the first end of the cap and a latch receiver that is positioned proximate the second end of the cap. In another aspect, the latch receiver includes a channel that is defined by substantially parallel channel walls. The channel is configured to releasably receive the latch. In another aspect, the latch includes a shaft that has an enlarged head positioned at the non-hinged end of the latch. The perimeter of the enlarged head is larger than the perimeter of the shaft. The head of the latch is configured to engage the channel and to be held in the channel. The width of the channel is smaller than the head of the latch. The channel walls are resilient such that the walls flex away from each other during receipt of the head of the latch. In another aspect, the coupling means include at least one latch that is pivotally coupled to the retainer. The at least one latch is configured to engage the cap. The at least one latch includes a projection that extends substantially orthogonally from the at least one latch and is configured to engage the cap. The cap includes at least one engagement portion fox receiving the projection on the at least one latch. In another aspect, the at least one latch is coupled to the retainer with a live hinge. In another aspect, the at least one latch includes a plurality of latches that are spaced along the periphery of the retainer. In another aspect, in a first position the at least one latch extends substantially laterally from the periphery of the retainer in a substantially planar relationship with the retainer. After placing the cap on the retainer, the at least one latch is rotated toward the cap to a second position in which the latch engages the cap to couple the retainer to the cap. In another aspect, the retainer includes at least one resilient snap far releasably coupling the retainer to the cap. The at least one snap extends from the outer periphery of the retainer in a substantially perpendicular direction from a substantially planar, annular surface of the retainer. Each of the at least one snaps has a projection extending substantially perpendicular and radially inwardly from the snap. The at least one snap is configured to deflect radially outwardly to slide over a corresponding lip portion of the cap when the cap and retainer are brought together in a mating relationship. The at least one snap is configured to return toward a neutral position after the projection on the at least one snap passes the lip portion of the cap such that the projection of the at least one snap engages a receiver portion of the cap. In another aspect, the planar, annular surface of the retainer is configured to secure the sleeve to the retainer. In another aspect, the retainer includes a sidewall portion adjacent to each of the at least one snaps and on either side of each of the at least one snaps. The cap includes openings disposed along the edges of the cap for receiving the sidewall portions of the retainer. In another aspect, the cap includes at least one snap for releasably coupling the cap to the retainer. The at least one snap extends perpendicularly from the periphery of the cap. The at least one snap is configured to engage with a corresponding lip portion of the retainer. Each of the at least one snaps has a projection extending substantially perpendicular and radially inward from the snap. The at least one snap is configured to deflect radially outwardly such that the projection on the at least one snap slides over the corresponding lip portion of the retainer when the cap and retainer are brought together in a mating relationship. The at least one snap is configured to return toward a neutral position after the projection on the at least one snap passes the lip portion of the retainer such that the projection of the at least one snap engages a lip portion of the retainer. In another aspect, the cap includes an inner cylindrical wall and the gel pad being coupled to the inner cylindrical wall. In another aspect, the gel pad is bonded to the inner cylindrical wall. In another aspect, the gel pad is molded to the cap. In another aspect, the surgical access device also includes a resilient fabric integrated on a surface of the gel pad and coupled to the periphery of the cap. In another aspect, the surgical access device also includes a first fabric integrated on a first surface of the gel pad and coupled to the periphery of the cap, and a second fabric integrated on a second, opposite surface of the gel pad and coupled to the cap. In another aspect, the surgical access device also includes a first fabric coupled to the periphery of the cap and a second fabric coupled to the cap a distance from the first fabric. The space between the first fabric and the second fabric defines a cavity. The gel pad is positioned within the cavity between the first and second fabric. In another aspect, the gel pad includes multi-cusped lobes. Adjacent lobes are configured to seal upon one another. In another aspect, the gel pad includes at least two concentric regions of differing resiliency. The at least two concentric regions include a first, central region having first resiliency and a second, outer region having less resiliency than the first region. In another aspect, the gel pad has more than two concentric regions having differing resiliency with the resiliency of each region decreasing in relation to the increase in distance from the first, central region. In another aspect, the gel pad includes gas-filled pockets arranged substantially around the center of the gel pad. In another aspect, the gel pad includes gas-filled pockets dispersed randomly throughout a region beyond the center of the gel pad.

These and other features of the invention will become more apparent with a discussion of the various embodiments in reference to the associated drawings.

DESCRIPTION

Figure 1:
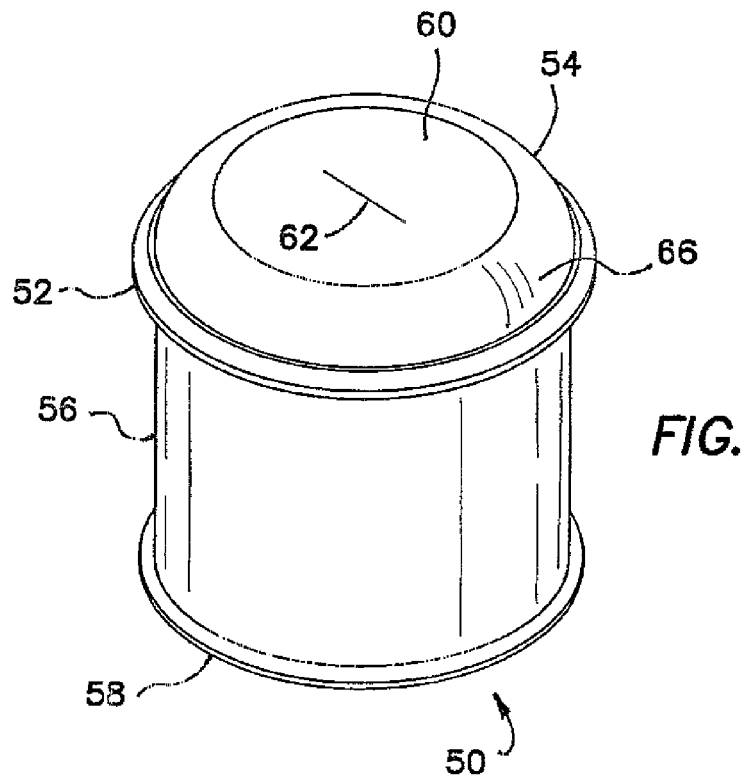
FIG. 1 depicts a top perspective view of a hand access laparoscopic device of the present invention.
Figure 2:
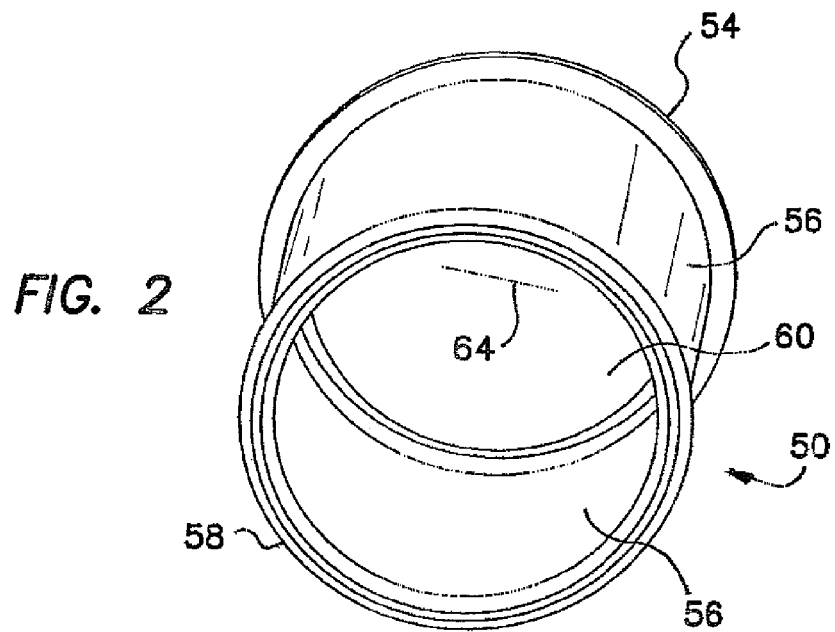
FIG. 2 depicts a bottom perspective view of the hand access laparoscopic device of FIG. 1.

In FIGS. 1 and 2, a surgical hand access device 50 according to one aspect of the present invention is shown. The device includes a retainer 52 and a cap 54. The cap 54 and the retainer 52 are both substantially annular and both include an opening therethrough. The retainer 52 is adapted to be placed against a body wall. The retainer 52, in one aspect, is rigid and is associated with and/or capable of being coupled to an elongate sleeve 56. The surgical hand access device 50 is adapted for disposition relative to an incision in a body wall. The surgical hand access device 50 also facilitates insertion of an instrument through the access device and maintenance of a sealing relationship with the instrument.

In one aspect, the elongate sleeve 56 extends through an incision to a point where an attached retention ring 58 contacts the interior portions of the body cavity and provides tension between the retainer 52 outside the body cavity and the retention ring. The retainer 52 in one aspect also supports or otherwise enables a portion of the elongate sleeve 56 to remain outside of the body cavity. Additionally, the retainer 52, retention ring 58 and elongate sleeve 56 together allow the incision to be retracted and isolated during a surgical procedure. In one aspect, the elongate sleeve 56 and aspects thereof is a wound retractor type device such as described in U.S. patent application Ser. No. 10/516,198, filed Nov. 30, 2004, the disclosure of which is hereby incorporated by reference as if set forth in full herein.

As shown, the retainer 52 and retention ring 58 are circular, but as one skilled in the art would appreciate, they may be of different shapes and sizes. The retainer 52 in one aspect may be either rigid, flexible or a combination of both. The retention ring 58 may be flexible to facilitate insertion into the body cavity. As will be described in more detail, the access device 50 includes coupling means that are adapted for coupling the cap 54 and the retainer 52 together.

A gel pad 60 may be coupled to, attached to, formed or integrated with the cap 54 so that a gas-tight conduit is formed between the cap and the sleeve 56. The gel pad 60 covers and seals the entire opening in the cap 54. In one aspect, the gel pad includes a plurality of intersecting dead-end slits 62, 64 that form an access portion or passage through the gel pad 60. Unlike foam rubber or other similar types of elastic materials, the gel pad 60 provides a gas tight seal around a variety of shapes and sizes of hands or instruments inserted therethrough.

In one aspect, the gel material from which the gel pad 60 is made is an elastomeric gel. Some such gels have been described in U.S. patent application Ser. No. 10/381,220, filed Mar. 20, 2003, the disclosure of which is hereby incorporated by reference as if set forth in full herein. The gel can be prepared by mixing a triblock copolymer with a solvent for the midblocks. The endblocks are typically thermoplastic materials such as styrene and the midblocks are thermoset elastomers such as isoprene or butadiene, e g., Styrene-Ethylene-Butylene-Styrene (SUBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651, which has a styrene to rubber ratio of 33/67. Once formed, the gel is substantially permanent and, by the nature of the endblocks, processable as thermoplastic elastomers henceforward. The mixture or slurry has a minimum temperature at which it becomes a gel, i.e., the minimum gelling temperature (MGT). This temperature, in one aspect, corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks distribute and form more rapidly.

The various base formulas may also be alloyed with one another to achieve a variety of intermediate properties. For example, KRATON G1701X is a 70% SEB 30% SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics that might provide the desired sealing qualities with the addition of a foaming agent. The silicone material may be of the types currently used for electronic encapsulation. The harder plastics may include PVC, Isoprene, KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing bonding sites or a surface charge. Additionally, oil based colorants may be added to the slurry to create gels of different colors.

In one aspect, the mixture/slurry used with the various embodiments of the caps that are described herein are composed of about 90% by weight of mineral oil and about 10% by weight of KRATON G1651. From a thermodynamic standpoint, this mixture behaves similar to mineral oil. Mineral oil has a considerable heat capacity and, therefore, at about 130° C. it can take 3 or 4 hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect, the gel may be air-cooled. Those familiar with the art will recognize that other cooling techniques that are well known in the art may be employed and are contemplated as within the scope of the present invention.

Many of the properties of the KRATON/oil mixture will vary with adjustments in the weight ratio of the components. In general, the greater the percentage of mineral oil the less firm the mixture; the greater the percentage of KRATON, the more firm the mixture. If the resultant gel is too soft it can lead to excessive tenting or doming of the gelcap during surgery when a patient's abdominal cavity is insufflated. Excessive tenting or doming may cause the slits 62, 64 to open, providing a leak path. Additionally, if the gel is too soft it might not provide an adequate seal. However, the gel should be sufficiently soft to be comfortable for the surgeon while simultaneously providing good sealing both in the presence of an instrument and in the absence of an instrument.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about 1.0 atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about 10% Degassing the slurry helps reduce the potential of the finished gel to oxidize.

Degassing the slurry tends to make the resultant gel firmer. A degassed slurry composed of about 91.6% by weight of mineral oil and about 84% by weight of KRATON G1651, an eleven-to-one ratio, results in a gel having about the same firmness as a gel made from a slurry that is not degassed and that is composed of about 90% by weight of mineral oil and about 10% by weight of KRATON G1651, a nine-to-one ratio.

Mineral oil is of a lighter density than KRATON and the two components will separate after mixing, with the lighter mineral oil rising to the top of the container. This separation may occur when attempting to form static slurry into gel over a period of several hours. The separation can cause the resulting gel to have a higher concentration of mineral oil at the top and a lower concentration at the bottom, e.g., a non-homogeneous gel. The speed of separation is a function of the depth or head height of the slurry being heated. The mass of slurry combined with the head height, the temperature at which the gel sets and the speed with which the energy can be transferred to the gel, factor into the determination or result of homogeneous gel versus a non-homogeneous gel.

Figure 3:
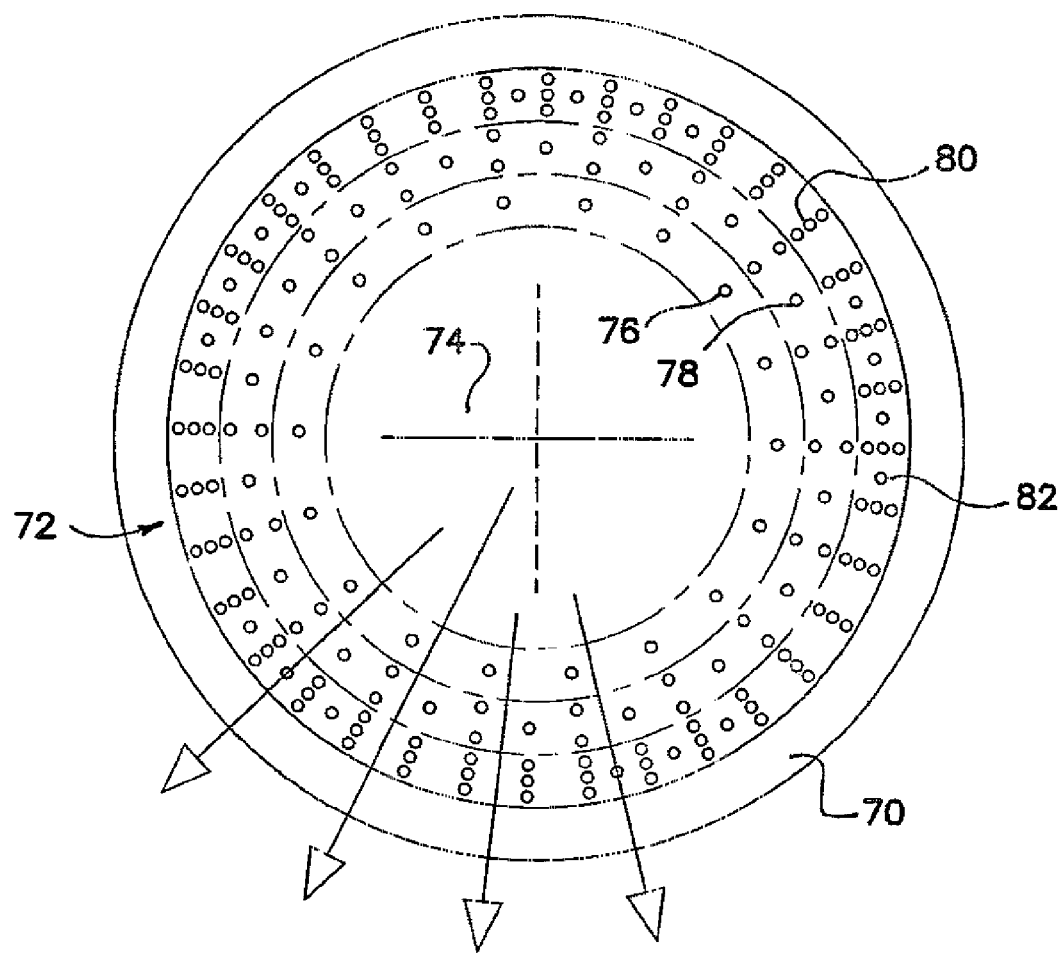
FIG. 3 depicts a plan view of a gelcap with a gel pad having regions of varying firmness.
Figure 4:
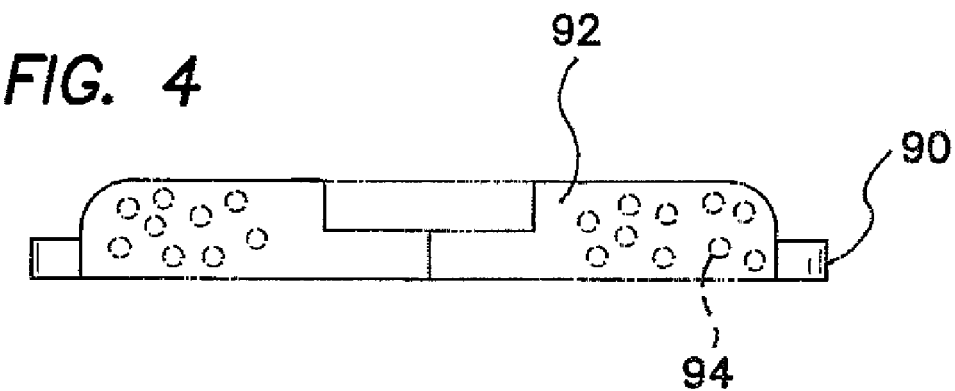
FIG. 4 depicts a side view of a gelcap with gel having gas-filled pockets disbursed therein.
Figure 5:
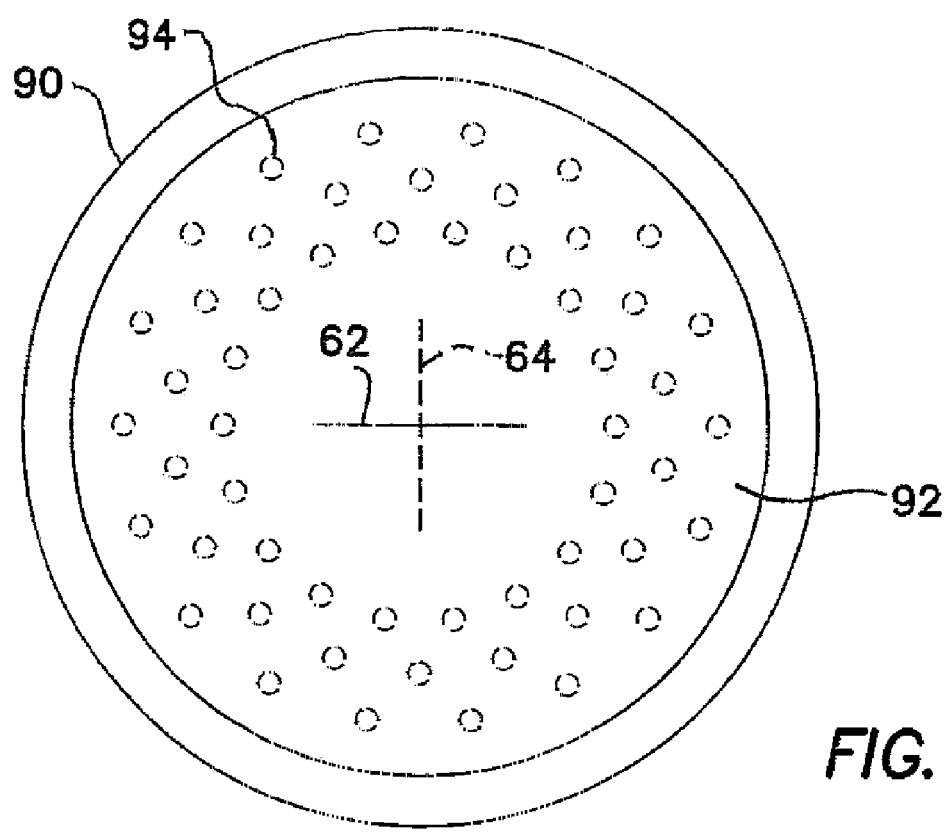
FIG. 5 depicts a plan view of a gelcap with gel having gas-filled pockets disbursed therein.
Figure 6:
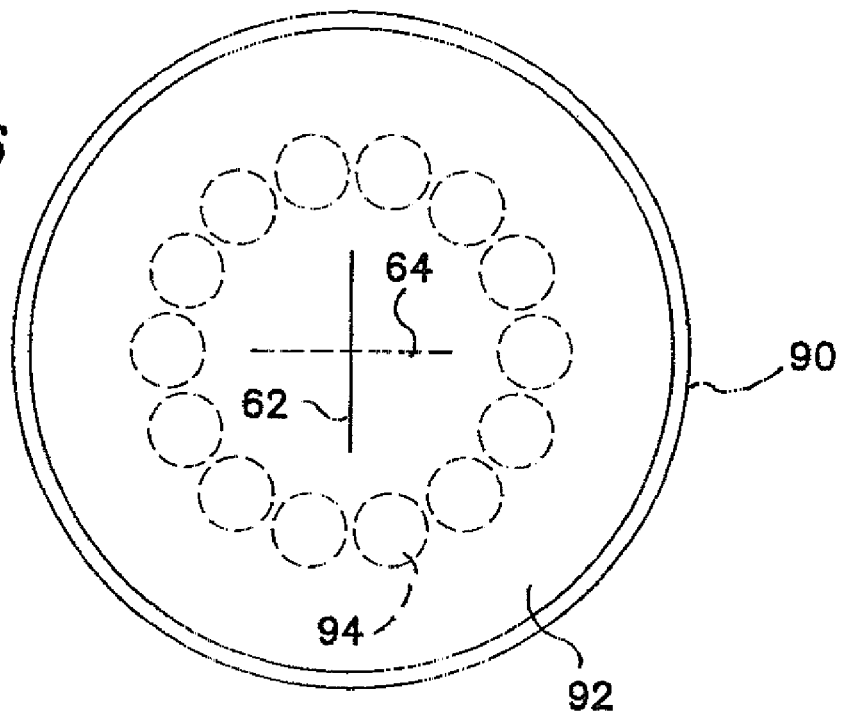
FIG. 6 depicts a plan view of a gelcap with gel having gas-filled pockets disbursed therein.
Figure 7:
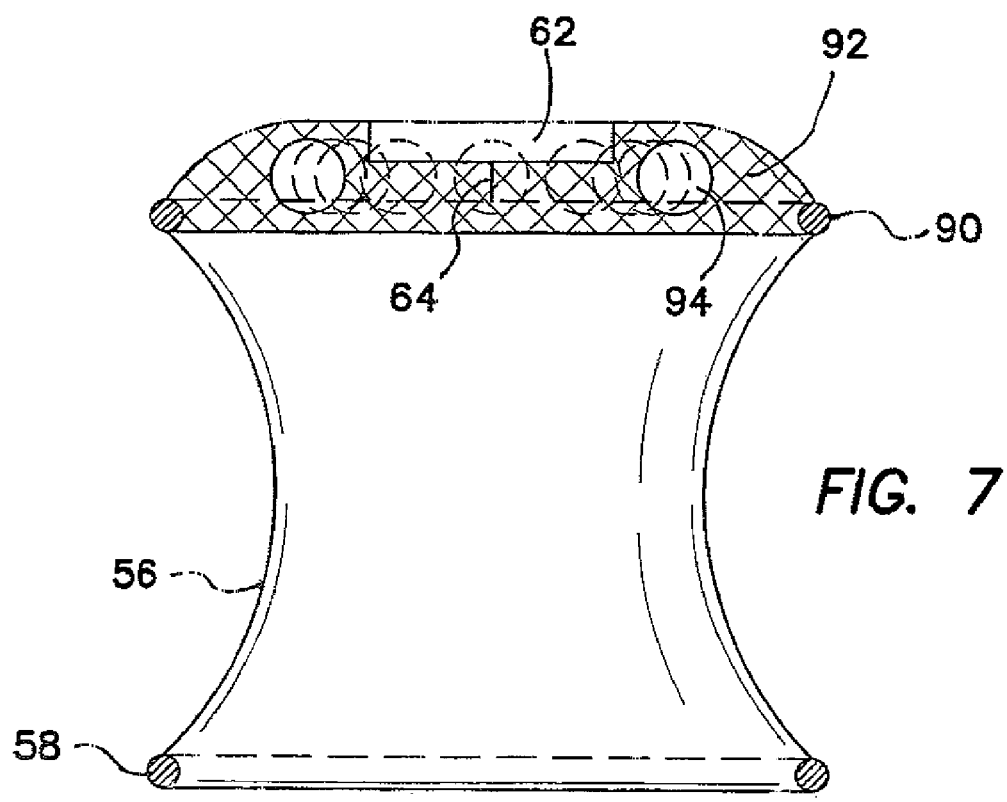
FIG. 7 depicts a side view of a hand access laparoscopic device including a gelcap with gel having gas-filled pockets disbursed therein.

One aspect of a cap 70 in accordance with the present invention is illustrated in FIG. 3 with a gel pad 72 that differs in texture in specific regions 74-80. For example, in one aspect, the gel pad 72 has a soft occlusive first, central sealing region 74, a second region 76 less resilient than the first region, a third region 78 less resilient than the second region, a fourth region 80 less resilient than the third region, and so-on. More particularly, the gel pad 72 may include more than two concentric regions having differing resiliency with the resiliency of each region decreasing in relation to the increase in distance from the first, central region 74. The progressively less resilient or pliable regions allow positive attachment of the gel pad 72 to a support structure, such as the cap 70, while preserving the desirable occlusive properties of a softer more resilient material at, or about, the central portion of the gel pad.

In one aspect, the gel pad 72 has gradient concentric portions 74-80 in which the gel pad is centrifugally molded or formed. During gel formation, the slurry is mixed in a centrifuge. By rotating the slurry while forming the gel pad 72, density separation is created in which denser triblocks of the slurry migrate towards the circumference of the container holding the spinning slurry and the mineral oil increases in concentration towards the center. In this manner, a firmer gel is formed on the exterior of the finished part and a softer gel is formed in the central portion of the finished part, which is useful in hand access seals for laparoscopic surgery.

In one aspect, a long flat rectangular part is used instead of a thin circular part. There are three conventional axes of rotation associated with the rectangular part. The first axis is through the center of the part normal to the long and short axes of the part. Rotation about the first axis induces a higher density gel at the ends of the part as will rotating the gel about the short midpoint of the rectangle. However, rotation about the long axis of the rectangle creates higher density gel along the long edges of the rectangle. The rotation can be altered during processing, as in the case of rotational molding, in which the part is rotated about multiple axes during processing. The axis of rotation does not have to intersect a centroid of the part or even be within the part itself.

A reverse texture layout of the gel pad 70 can be achieved by selecting lighter density triblocks and higher density mineral oils. Other components can be added as well, based on the desired effect, including additives such as colorants, inert filler material, different oils, different triblock or diblock copolymers, polymers, plasticizers, decorative items, etc.

In one aspect, heavy plastic components 82 are provided with the gel pad 72 or slurry and gravitate toward outer regions of the gel away from the center, leaving the central region 74 with a particular proportion of plastic material and oil. The outer regions 76-80 of the gel pad 72 are denser and contain more heavy plastic material than the central region 74. When the particular gradient proportions for the gel pad 72 are achieved, rotation is slowed and the gel pad is allowed to cool.

In one aspect, a non-homogenous gel pad with soft gel on one side and a firmer gel on the other is accomplished with density separation over time commensurate with the timing of the energy input into the gel which can vary with the direction of gravity.

In FIGS. 4-7, a cap 90 includes a gel pad 92 with a plurality of gas-filled pockets 94. The pockets 94 may be formed by the presence of lightweight foam or balloons, or by casting or molding the gel around spheres or solid objects of other shapes that are removed after the gel pad 92 has cured. The foam, balloons, spheres or other shapes may be inserted into the mold cavity either prior to or after filling the mold cavity with the slurry. In one aspect, the arrangement of gas-pockets 94 substantially around the center of the gel pad 92 reduces the weight of the gel pad and resistance to the passage of a surgeon's hand or instruments while retaining occlusive properties. An alternative aspect of the gel pad 92 contemplates a more random dispersion of gas pockets 94 throughout the region beyond the center of the gel pad, which reduces the overall weight of the gel pad.

The gel pad or gelcap in various aspects of the present invention may be gamma sterilized. The relative or comparative simplicity of qualifying the sterilization process, for example of gamma versus ethylene oxide, of the gel pad and the device with the gel pad is desirable. However, under gamma sterilization large bubbles can form in the gel pad causing potential cosmetic or aesthetic issues in the sterilized devices. The bubbles are more than 99% room air, so removal of the dissolved air in the slurry is performed prior to forming the slurry into gel. For example, the slurry may be degassed via vacuum, as described above, and turned into gel by heat. Bubbles may still form in the gel during gamma sterilization but disappear in a period of about 24 to 72 hours. In one aspect, the percentage of dissolved gas in the mineral oil at room temperature is about 10%. The removal of the air in the gel has an additional effect of making the gel firmer. This however is counterbalanced by the softening effect on the gel caused by gamma radiation during gamma sterilization.

If the gel pad is to be gamma sterilized, the gel may include about 90% mineral oil by weight and about 10% KRATON by weight. As stated above, degassing the slurry has the effect of making the gel firmer. However, the gamma radiation softens the gel to substantially the same firmness as a gel having about 90% mineral oil by weight and about 10% KRATON by weight that is not degassed and gamma sterilized.

In one aspect, cyanoacrylate, e g., SUPERGLUE or KRAZY GLUE, may be used to bond or otherwise couple or attach the gel pad 60 to the cap 54. The glue may attach to either the rubber or styrene component of the tri-block and the bond is frequently stronger than the gel material itself. In another aspect, a solvent may be used to dissolve the plastics in the cap and the polystyrene in the gel. The solution of solvent is applied to the gel pad and cap in either a spray or dip form. In effect, the solution melts both the plastic of the cap as well as the polystyrene in the gel pad to allow a chemical bond to form between the two, which remains when the solvent evaporates.

Polyethylene can be dissolved in mineral oil and then applied to the gel pad. The mineral oil will not evaporate but will over time absorb into the gel pad and impart a polyethylene layer on the gel pad that may have some beneficial properties.

In one aspect, the gel pad 60 is cast into a DYNAFLEX or KRATON polymer support structure, e.g., the cap 54. By using KRATON polymer or a similar material in the cap, ring adhesion between the gel pad 60 and the cap 54 can be achieved. The polystyrene in the gel is identified as achieving adhesion with polyphenylene oxide (PPO), polystyrene and other polymers.

In the casting process the gel pad 60 and the cap 54 are heated to a temperature above about 130° C. and held at that temperature for several hours, e.g., about 3 to 4 hours. The temperature used is not sufficient to deform the cap 54.

The cap 54, in one aspect, includes a polymer, e.g , polyethylene (PE). In one aspect, the polyethylene is a low density polyethylene (LDPE) or high density polyethylene (HDPE), or ultra high molecular weight polyethylene (UHMWPE). In one aspect, the cap 54 may be made of a polymer, such as polycarbonate and may be fabricated by methods including injection molding.

The gel includes mineral oil. PE has a higher molecular weight than mineral oil. PE is dissolved by mineral oil at high temperatures. As such, as the PE and the mineral oil in the gel pad 60 intermix as both are heated to and held at temperatures above about 130° C., a bond between the PE and gel pad is formed.

In one aspect, the cap 54 includes polycarbonate. The polycarbonate of the cap 54 does not form bonds with the gel pad 60 at 130° C. However, by raising the temperature to about 150° C. for a few minutes during casting, bonding occurs between the gel pad 60 and the cap 54. As such, heating the gel pad 60 and cap 54 to temperatures at which both the polystyrene of the gel and the polycarbonate are simultaneously beyond their melt points allow bonds to form between the gel pad and the cap. Alternatively, the gel pad 60 and cap 54 may be heated to near or at the glass transition temperature of the polycarbonate cap to form the bond between the gel pad and the cap.

Figure 8:
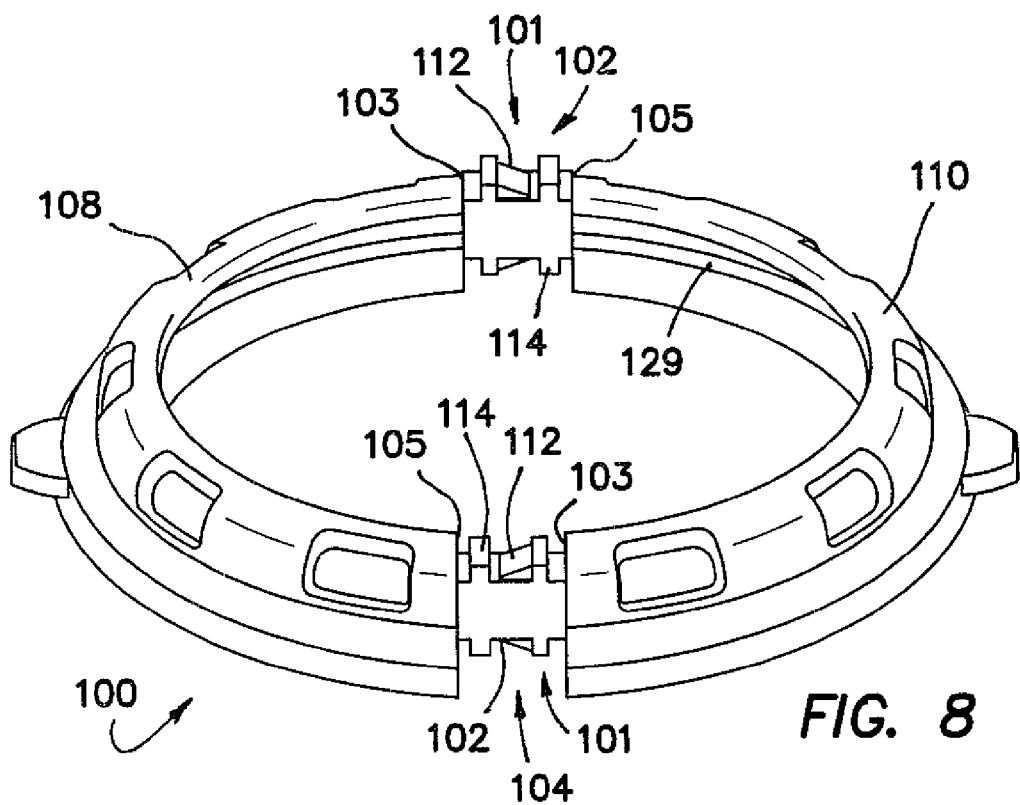
FIG. 8 depicts a top perspective view of a multiple-piece cap having squeeze release buckle connectors molded into the ends of the pieces forming the cap.
Figure 9:
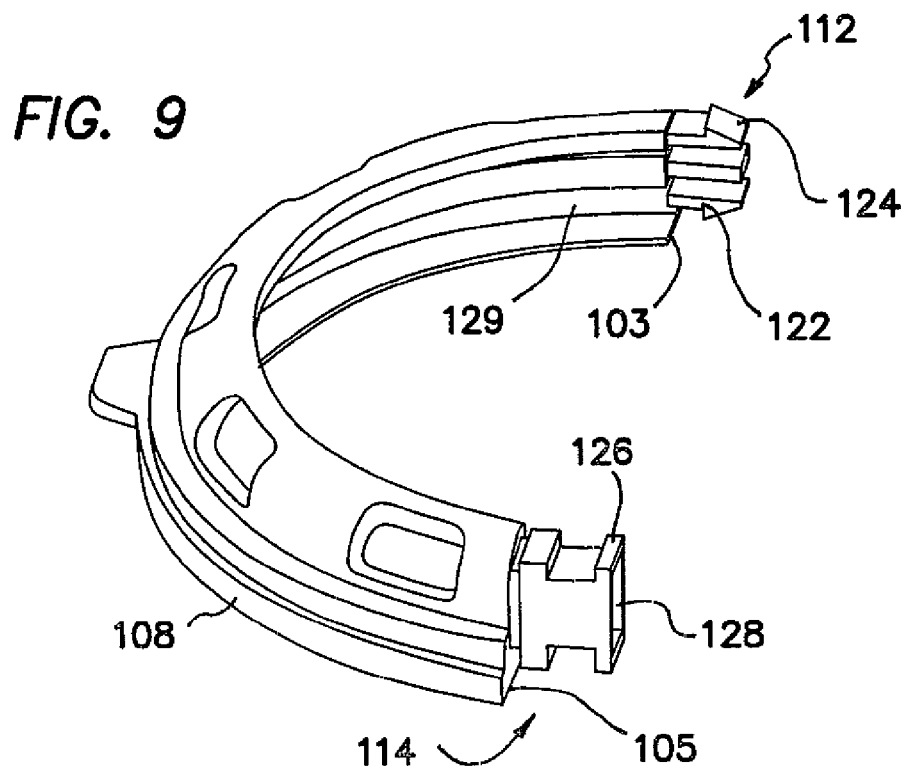
FIG. 9 depicts a top perspective view of one of the pieces of the cap having a male squeeze release buckle connector fitting at one end and a female squeeze release buckle connector fitting at the other end.
Figure 10:
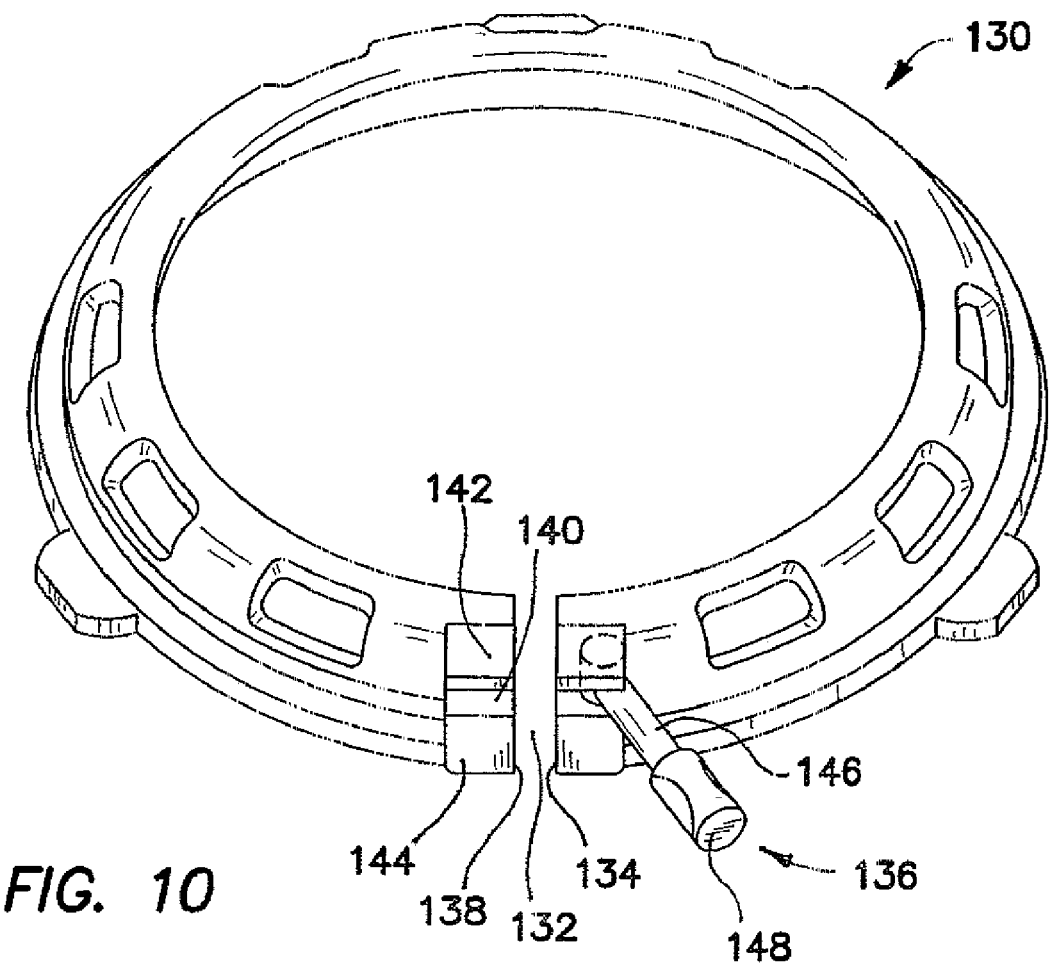
FIG. 10 depicts a top perspective view of a cap having a gap with a latch pivotally coupled on one side of the gap and a groove for accepting the latch on the other side of the gap.

Referring to FIGS. 8-10, the cap 100, 130 includes at least one gap 101, 132 along the annular perimeter of the cap. The at least one gap 101, 132 creates at least one first end 103, 134 and at least one second end 105, 138 of the cap 100, 130. The gap 101, 132 facilitates a transition in the cap from a first, larger periphery to a second, smaller periphery. As will be discussed in more detail below, the cap 100, 130 includes means for maintaining the cap at the second, smaller periphery. When the cap 100, 130 is set at the first, larger periphery, the retainer 52 (FIG. 1) may be inserted into or removed from the opening of the cap. The retainer 52 (FIG. 1) may be fixedly coupled to the cap 100, 130 by transitioning the perimeter of the cap to the second, smaller periphery while the retainer is positioned within the opening of the cap, and maintaining the periphery of the cap at the second, smaller periphery with the maintaining means.

Referring to FIGS. 8-9, the cap 100 incorporates squeeze release buckles 102 molded into or otherwise coupled to the cap. The cap 100 includes a first arc 108 and a second arc 110, the first and second arcs being separated by first and second gaps 101. The first arc 108 has a first barbed portion 112 extending from a first end and adapted to be inserted in a snap fit mating relationship with a second, receiver portion 114 extending from a second end of the second arc 110, thereby coupling the at least one first end 103 of the cap 100 to the at least one second end 105 of the cap. Another barbed portion 112 may extend from the first end of the second arc 110, which is operationally inserted in a snap fit mating relationship with another receiver portion 114 extending from the second end 105 of the first arc 108. In another aspect, the first arc 108 has a barbed portion 112 on each end of the arc with the second arc 110 having corresponding receiver portions 114 on each end of the second arc.

With the first and second arcs 108, 110 placed adjacent to each other, such that the first end 103 of the first arc corresponds with the second end 105 of the second arc and the second end 105 of the first arc corresponds with the first end 103 of the second arc, and prior to being snapped together, the arcs define a first, larger periphery to allow placement of a retainer 52 (FIG. 1) between the two arcs. The barbed portions 112 engage with corresponding receivers 114 coupling the arcs together. Each barbed portion has a plurality of resilient arms 122, two of which have projections 124 extending therefrom. Each receiver 114 has corresponding sidewalls 126 for engaging projections 124 from the barbed portion, which causes the arms 122 to flex towards each other as the arms slide into a channel 128 defined by the receiver. As the projections 124 clear the ends of the sidewalls 126, the arms 122 are allowed to flex away from each other. Engagement or contact between the edges of the projections 124 with edges of the end of the sidewall 126 prevents the arcs 108, 110 from being detached from each other. By coupling the two arcs 108, 110 together, the delimited circumference is reduced to a second, smaller periphery to capture or hold the retainer 52 (FIG. 1). Flexing the arms 122 toward each other allows the barbed portions 112 to disengage from the sidewalls of the corresponding receiver 114 and to slide out from the receiver, thereby allowing the arcs 108, 110 to separate and detach from the retainer 52 (FIG. 1).

Although not shown, additional barbed portions and receiver snap engagements may be included in each arc to assist in the coupling between the cap 100 and the retainer 52 (FIG. 1) or allow for other size and shape configurations of the cap and/or retainer. In one aspect, the cap 100 includes a single gap 101 and a single barbed portion 112 and receiver portion 114 is provided. In one aspect the cap 100 having the single barbed portion 112 and receiver portion 114 may be provided with a hinge or pivot on another portion of the arc.

Referring now to FIG. 10, a cap 130 has a gap or opening 132 along a portion of the periphery of the cap. A latch 136 is hinged or pivotally coupled to the cap proximate a first end 134 of the opening 132 of the cap 130. Proximate a second, opposite end 138 of the opening 132, a latch receiver, such as an aperture or channel 140 defined by substantially parallel channel walls 142, 144, is configured to releasably receive the latch 136. The latch 136 has a shaft 146 coupled to the cap 130 on one end and an enlarged or bulbous head 148 having a perimeter or diameter larger than the perimeter or diameter of the shaft on the non-hinged end of the latch. The head 148 of the latch 136 is configured to be graspable and the latch swung so that the head may engage and be held in the channel 140 defined by the channel walls 142, 144. The width of the channel 140 is smaller than the diameter of the head 148 of the latch 136 and the channel walls 142, 144 are resilient such that the walls flex away from each other during receipt of the head of the latch. Alternatively, or additionally, portions of the head 148 may compress so that the head may be received and held in the channel 140. In one aspect, one or more projections extend from one or both channel walls 142, 144 and engage notches in the head 148, or vice versa, to secure the latch 136 to the channel 140.

In this manner, with the latch 136 open or not engaged with the channel 140, the initial periphery of the cap 130 allows simple placement of the retainer 52 (FIG. 1) within the periphery of the cap. Actuating the latch 136 closes the cap 130 and reduces the size of the periphery delimited by the cap, thereby securing the cap to the retainer 52 (FIG. 1).

Referring back to FIGS. 8-10, with the cap 100, 130 being separable or otherwise disjointed, placement of the respective retainer 52 (FIG. 1) within the inner periphery of the cap is eased. Subsequent joining or recoupling of the cap together secures the retainer and cap to each other. As such, one skilled in the art would recognize that other types of couplings or engagements may be used to couple or join separate portions of the cap and/or the retainer together to close or delimit a periphery to encase or otherwise secure the cap and the retainer together and vice versa. In one aspect, the retainer, or both the retainer and the cap, are separable, having couplings and/or engagements to recouple the separate portions together to secure the cap and retainer to each other.

Figure 11:
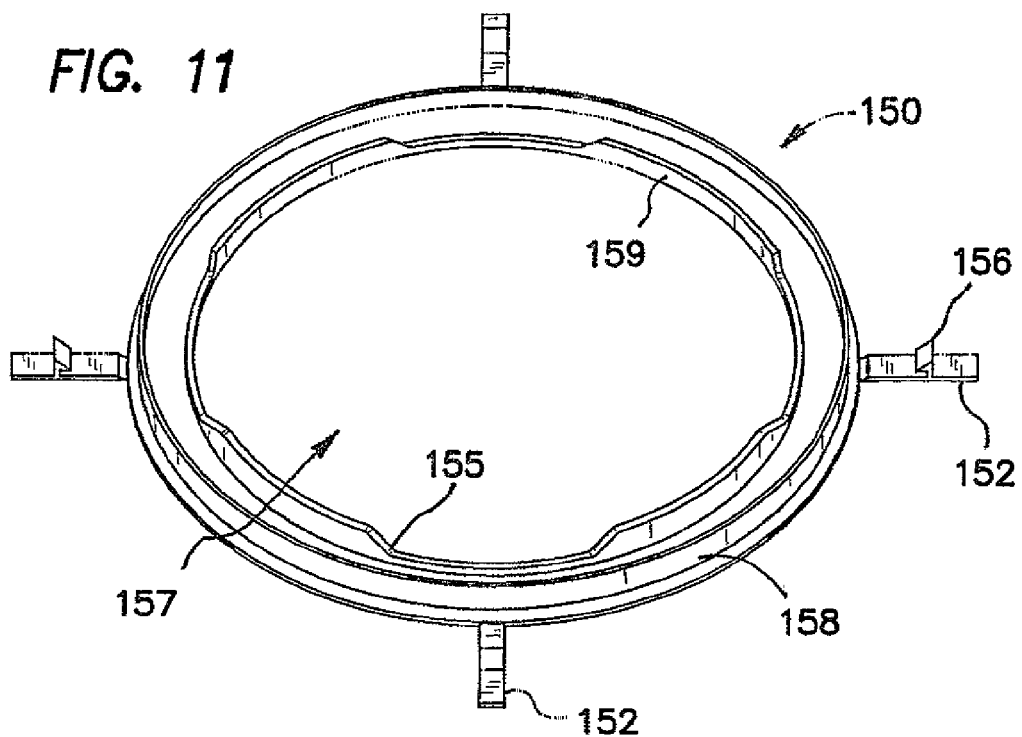
FIG. 11 depicts a top perspective view of a cap having latches for releasable coupling the cap to a retainer.
Figure 12:
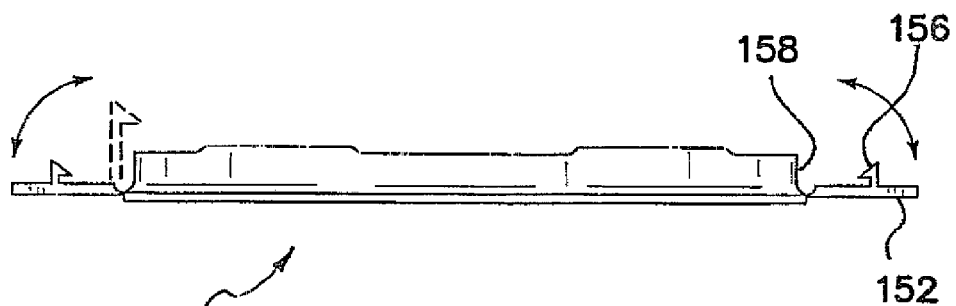
FIG. 12 depicts a side view of the cap of FIG. 11.
Figure 13:
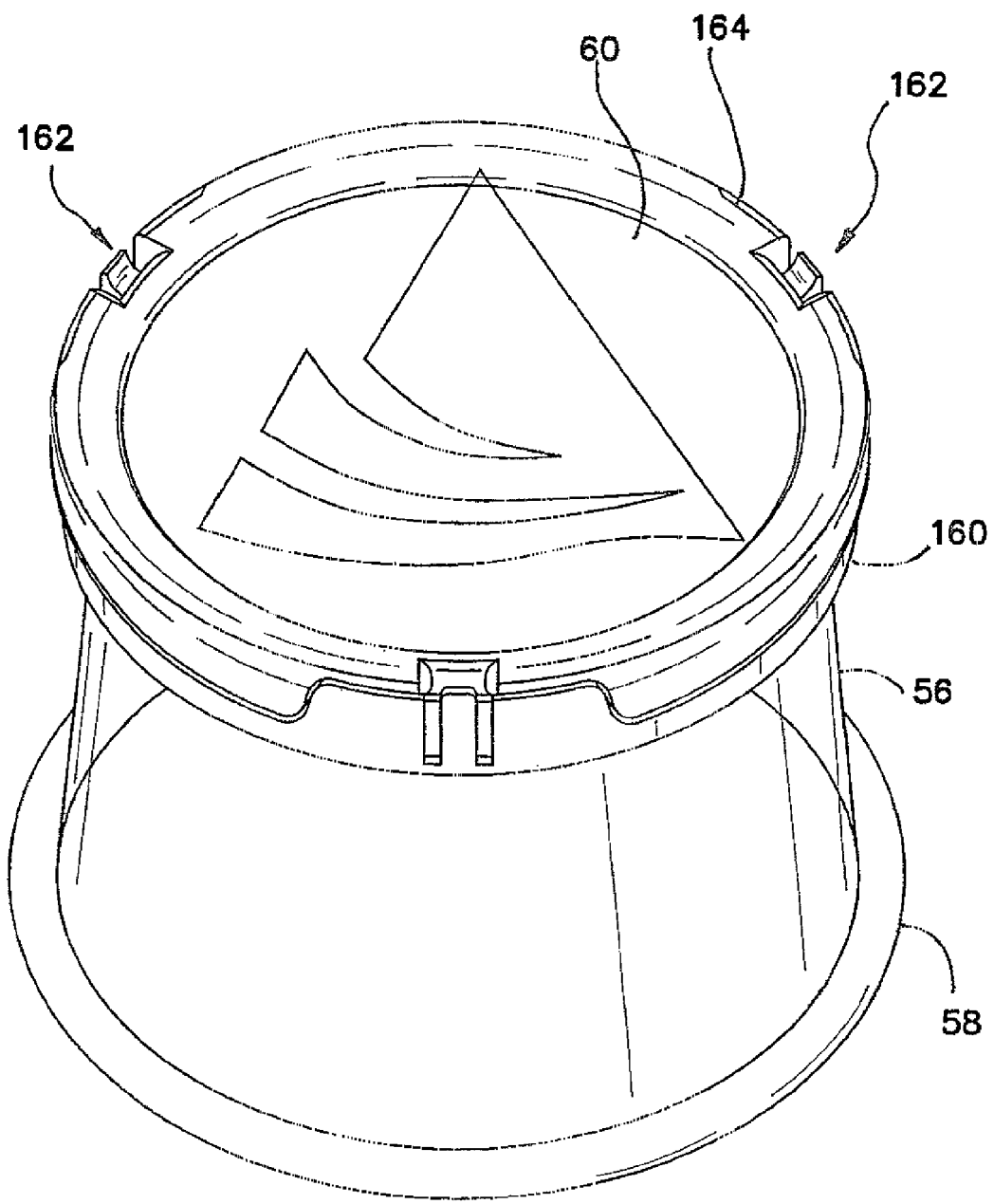
FIG. 13 depicts a top perspective view of a hand access laparoscopic device of the present invention including a cap and a retainer, the retainer having a plurality of snaps for releasably coupling the retainer to the cap.
Figure 14:
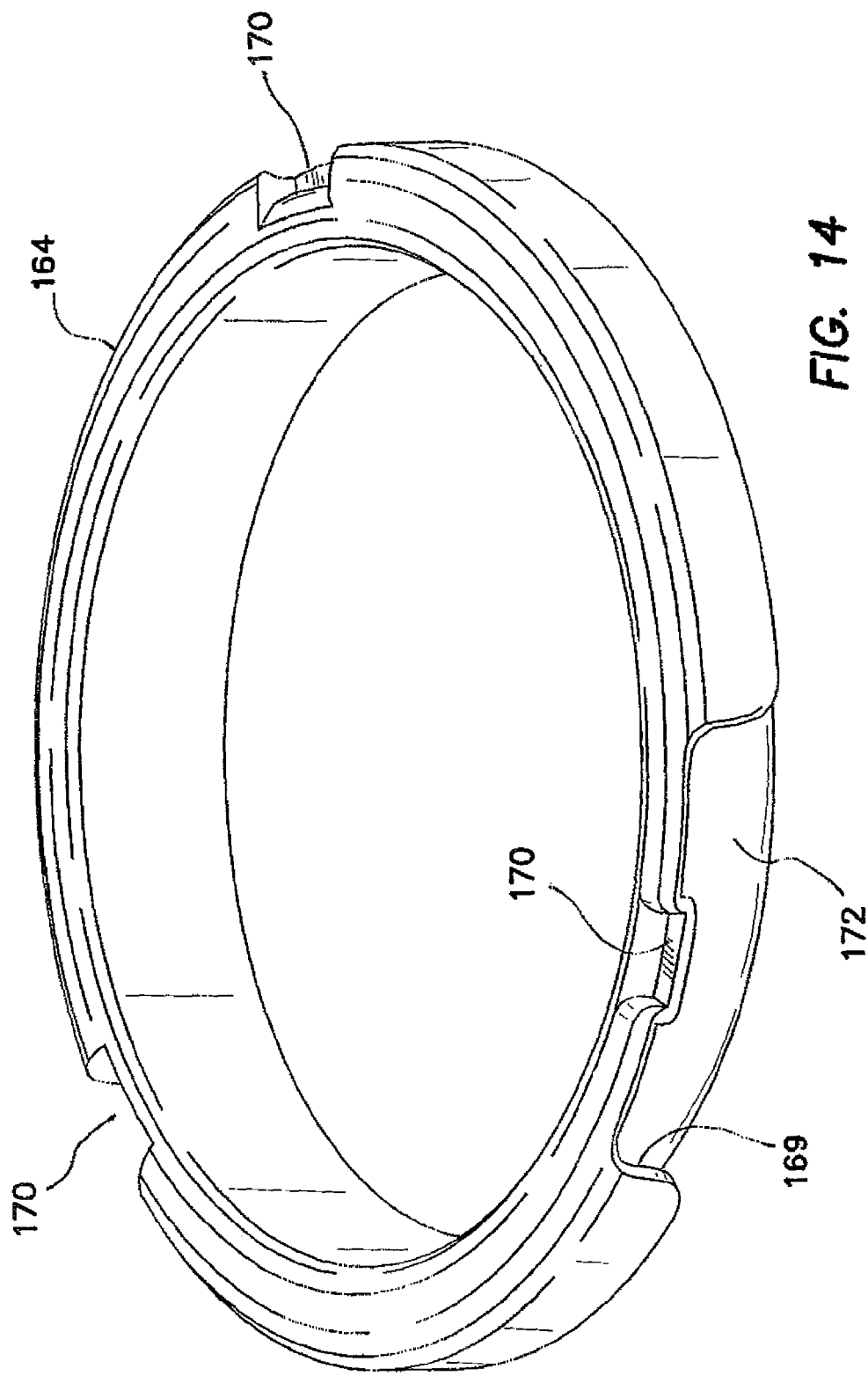
FIG. 14 depicts a top perspective view of the cap of FIG. 13.
Figure 15:
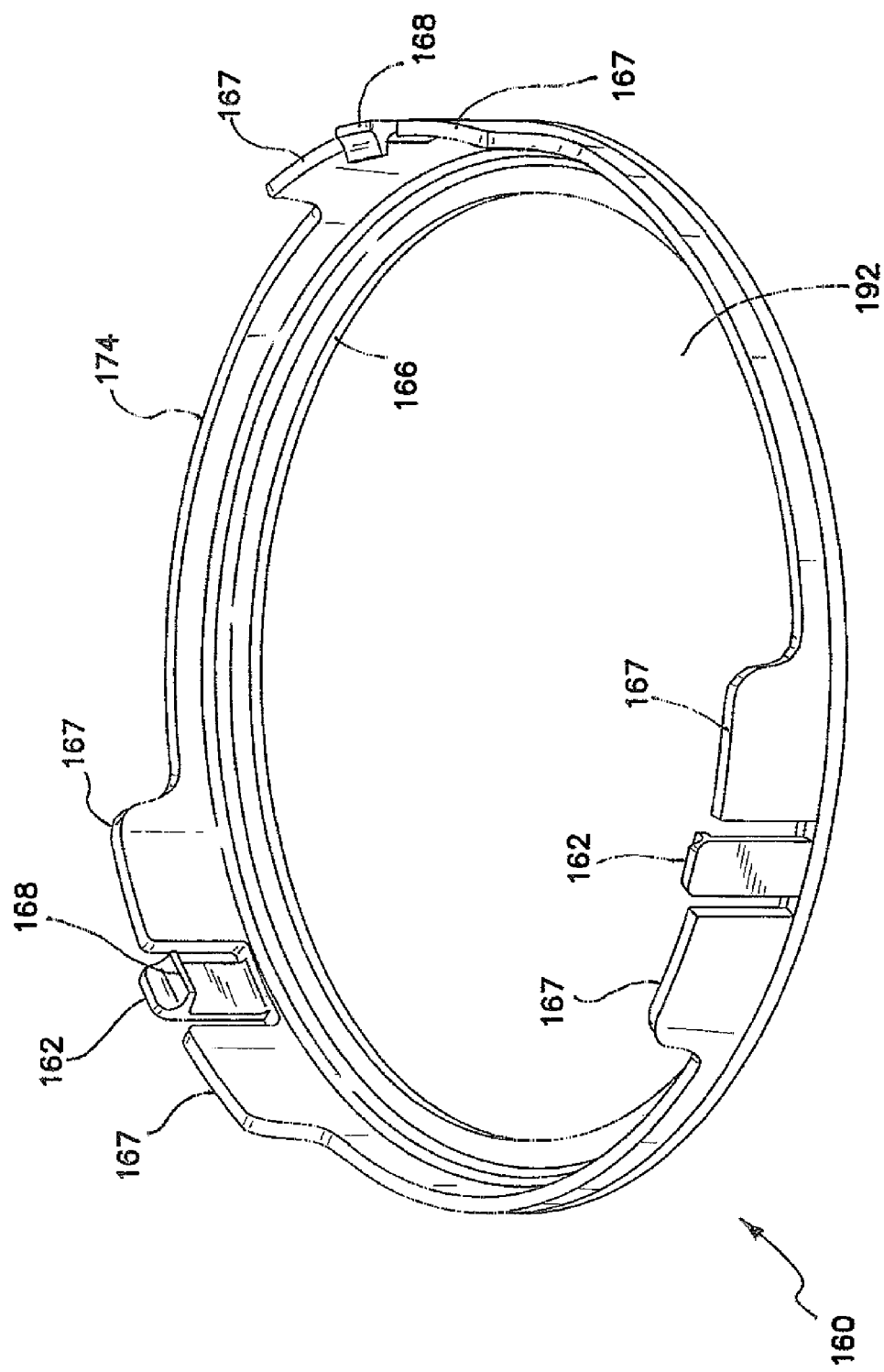
FIG. 15 depicts a top perspective view of the retainer of FIG. 13.
Figure 16:
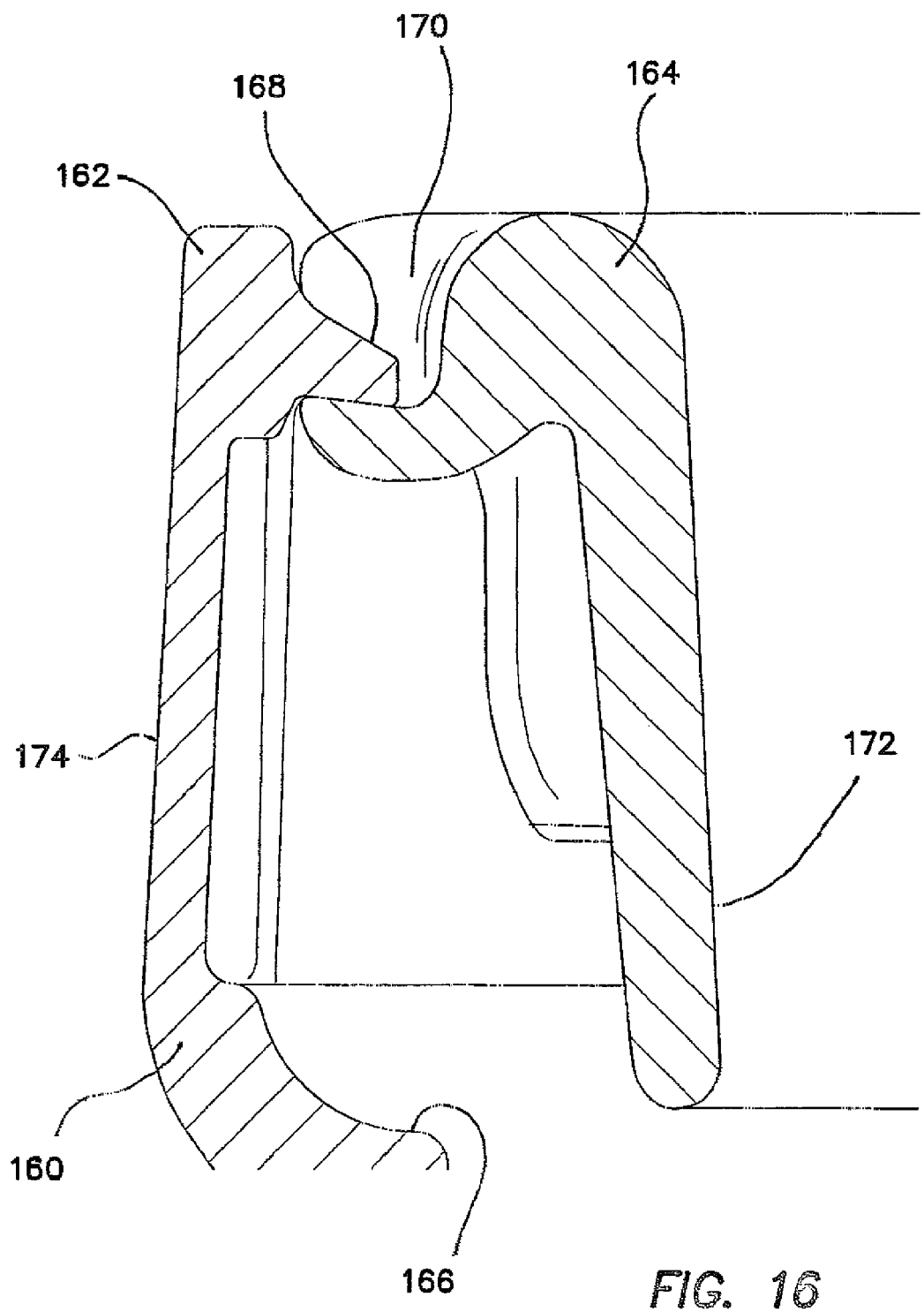
FIG. 16 depicts a section view depicting the interaction between the cap and the retainer of FIG. 13.
Figure 17:
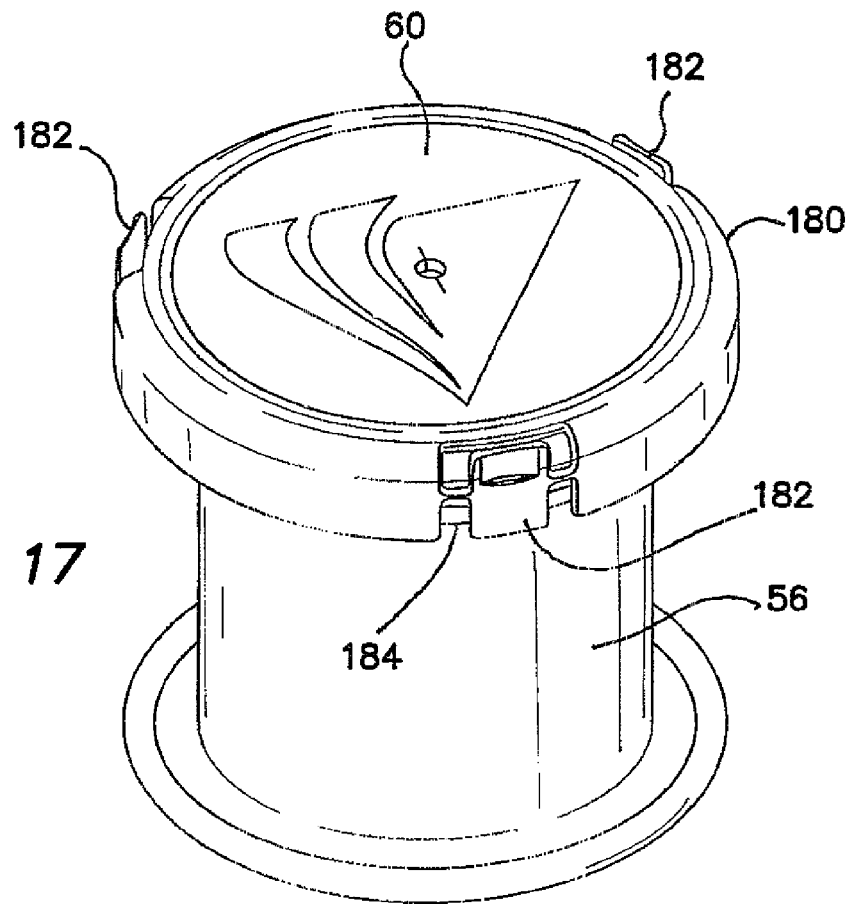
FIG. 17 depicts a top perspective view of a hand access laparoscopic device of the present invention including a cap and a retainer, the cap having a plurality of snaps for releasably coupling the cap to the retainer.
Figure 18:
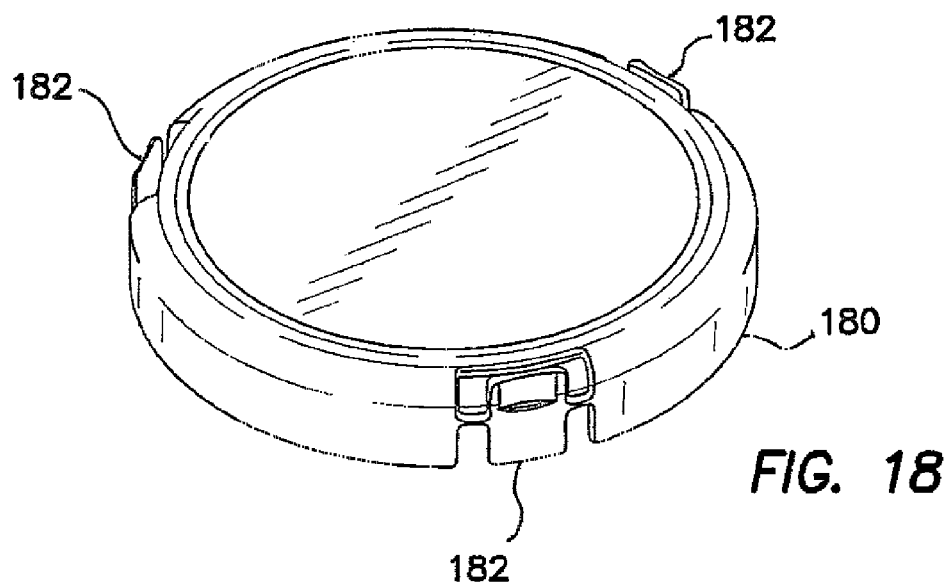
FIG. 18 depicts a top perspective view of the cap of FIG. 17.
Figure 19:
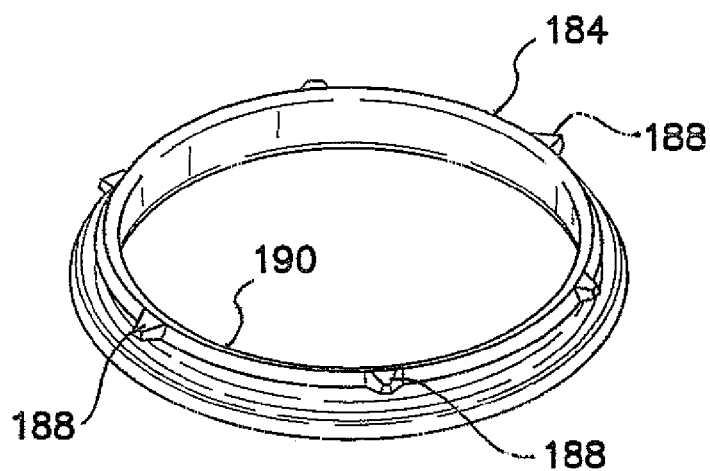
FIG. 19 depicts a top perspective view of the retainer of FIG. 17.
Figure 20:
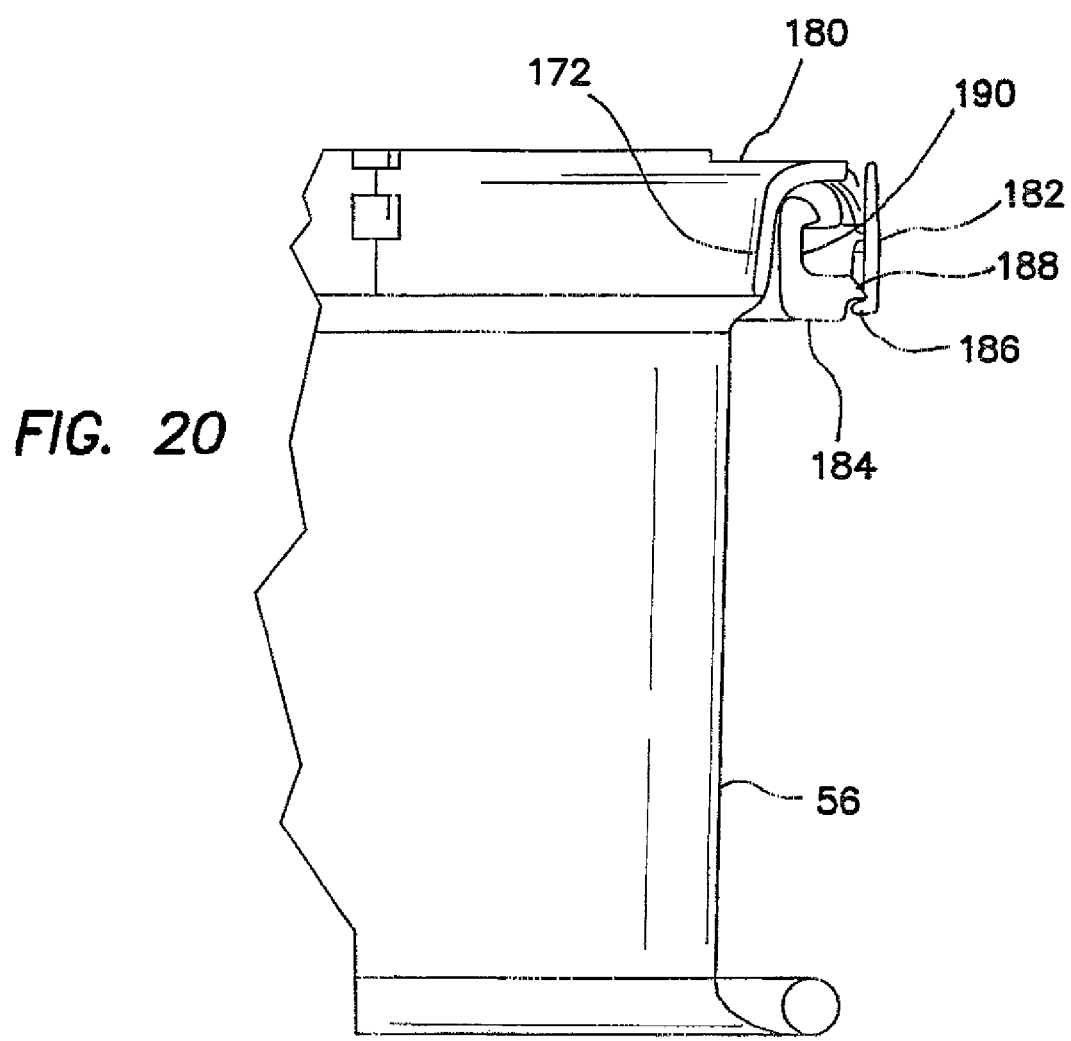
FIG. 20 depicts a section view depicting the interaction between the cap and the retainer of FIG. 17.

In FIGS. 11-12, the retainer 150 has one or more latches 152 to releasably couple the retainer to a cap 54 (FIGS. 1 and 2). In one aspect, a plurality of latches 152 is spaced along the periphery of the retainer 150. The latches 152 are hinged or pivotally coupled to the retainer 150 and are spaced along the periphery of the retainer. In one aspect, each of the latches is coupled to the retainer 150 with a live hinge. In a first position, the latches 152 extend laterally from the periphery of the retainer 150 in a substantially planar relationship with the retainer. Each latch 152 has a projection 156 extending substantially orthogonally from the latch. After placing or fitting the cap 54 on the retainer 150 and/or vice versa, the latches 152 are actuated to couple the cap and retainer together. In particular, the latches 152 are rotated toward the cap to a second position in which the latches engage a portion or edge of the cap 54 to couple the retainer to the cap. In one aspect, the engagement portion of the cap 54 is an opening, aperture, notch, step, projection or other similar type of receiver or engagement to secure the projection of the latch 152 to the cap.

In one aspect, one or more of the latches 152 has notches or openings for receiving corresponding projections or protrusions extending laterally from the cap 54 to couple the retainer 150 to the cap. Additionally or alternatively, although not shown, the cap may have one or more latches hinged along the periphery of the cap for engagement with portions or edges of the retainer to releasably couple the cap and retainer together.

Referring now to FIGS. 13-16, the retainer 160 has one or more resilient snaps 162 for releasably coupling the retainer and a cap 164 together. The snaps 162 extend from the outer periphery or edge of the retainer 160 in a substantially perpendicular direction from a substantially planar, annular surface 166 of the retainer. The planar, annular surface 166 of the retainer 160 secures the sleeve 56 (FIGS. 1 and 2) to the retainer. In one aspect, the surface 166 has projections or hooks to catch and secure the sleeve 56 to the retainer 160 under tension. The edge of the retainer 160 is also slightly raised to assist in the holding of the sleeve 56 and the handling of the retainer.

Multiple snaps 162 may be spaced along the periphery of the retainer 160. In one aspect, portions of the edge of the retainer 160 adjacent to each snap are elevated, thereby forming sidewall portions 167 on either side of each snap. The sidewall portions 167 protect the snaps 162 and strengthen or bolster the coupling between the retainer 160 and the cap 164 once coupled together. Additionally, the sidewall portions 167 facilitate handling and coupling the retainer 160 to the cap 164. Corresponding openings or cutouts 169 are disposed along the edges of the cap 164 to receive the sidewall portions 167 of the retainer 160

Each snap 162 also has a projection 168 extending substantially perpendicular and radially inwardly from the snap. After placing or fitting a cap 164 on the retainer 160 and/or vice versa, both are squeezed together. The snaps 162 are configured to flex or deflect radially outwardly to slide over a corresponding receiver portion 170, such as a lip portion or an edge, of the cap 164 when the cap and retainer are brought together in a mating relationship. The snaps 162 are also configured to return toward a neutral position after the projection 168 on the snaps pass the receiver portion 170 of the cap 164 such that the projection of the snaps engages the receiver portion 170 of the cap. The receiver portion 170 in one aspect has an opening, aperture, notch, step, projection or other similar type of receiver or engagement means to secure the projection 168 of the snap 162 to the cap 164. Alternatively, one or more of the snaps 162 have notches or openings (not shown) for receiving corresponding projections or protrusions (not shown) extending from the cap to secure the snaps of the retainer 160 to the cap 164. The cap 164 and retainer 160 may each be made via injection molding. Additionally, the cap 164 and retainer 160 may each be made of a polycarbonate material.

In one aspect, as shown in FIGS. 17-20, a cap 180 has one or more snaps 182 for releasably coupling the cap to a retainer 184. The snaps 182 extend perpendicularly from the periphery of the cap 180 for engagement with portions 188, such as corresponding lip portions, and/or edges of the retainer 184. Each snap 182 has a projection 186 extending substantially perpendicular and radially inwardly from the snap. After placing or fitting the cap 180 on the retainer 184, both are squeezed together. The snaps 182 flex or deflect radially outwardly to slide over the lip or edge 188 of the retainer 184 when the cap 180 and retainer are brought together in a mating relationship, thereby securing the cap, retainer and sleeve 56 disposed therebetween. Each snap 182 is configured to return toward a neutral position after the projection 186 on the snap passes the lip portion 188 of the retainer 184 such that the projection of the snap engages the lip portion of the retainer.

Referring now to FIGS. 1-20, the retainers and caps previously described in one aspect are rigid, thereby providing manufacturing benefits as well as easing the assembly of the device. In one aspect, the caps 54, 70, 90, 100, 130, 164, 180 also incorporate an inner cylindrical wall 172 (see FIG. 14) to which the gel pad 60 is bonded or otherwise coupled or attached to the cap. In this manner, the gel pad 60 attaches to a "skeleton" inside the sleeve 56 and provides a sealing area between the device and the wound, incision and/or body cavity. The coupling or intersection of the sleeve, cap and retainer together also provides another sealing area between the device and the body.

By securing the gel pad 60 to the inner cylindrical wall 172, the thickness of the gel pad and corresponding cap 54, 70, 90, 100, 130, 164, 180 is minimized along with the overall footprint of the device. A reduced thickness and overall size of the device provides a lighter device and allows for easier hand exchanges. With the gel pad thickness reduced and the gel pad being able to be substantially flush or recessed in the cap, the "doming" phenomena produced by gas pressure exerted on the body and device during insufflation is also reduced.

In various aspects (FIGS. 11-20) in accordance with the present invention, the retainer 150, 160 has a raised edge 158, 174 disposed around the outer periphery of the retainer. A raised edge 159, 190, in one aspect, is also disposed around the inner periphery of the retainer 150, 184. The inner periphery defines an opening 157, 192 through which the sleeve extends. The outer raised edge 158, 174 assists in maintaining or securing the releasable coupling between the cap and the retainer. In one aspect, a groove 129 (FIG. 8) extends along the circumference of the cap for receiving the outer raised edge to further enhance the coupling between the cap and retainer. Similarly, the inner raised edge assists in maintaining or securing the releasable coupling between the retainer and the sleeve. The inner raised edge also facilitates the seal between the inner cylindrical wall and/or gel pad, the sleeve and the retainer. In one aspect, notches or spaced valleys or openings 155 (FIG. 11) are disposed along the inner raised edge 159, which facilitates the engagement of the inner cylindrical wall and/or gel pad with the retainer by reducing binding between the components.

Several of the above-described attachments could be modified to integrate the retainer or a retainer like component directly into a sleeve to which the cap is releasably coupled. Similarly, the cap may be integrated directly into the retainer and/or sleeve creating a non-releasable coupling between the components.

In one aspect, casting the gel pad 60 into the cap 54 to form a gelcap 66 includes placing the cap into a mold cavity of a casting mold. The mold cavity may include support for the annular walls of the cap 54. The mold may be made of aluminum, copper, brass, or other mold material having good heat dissipation properties. However, those familiar with the art will recognize that other mold materials having lower heat dissipation properties will produce acceptable parts and these are contemplated as within the scope of the present invention as well.

The mold cavity having the cap 54 is filled with the slurry such that the slurry is in contact with the cap. To facilitate filling voids in the mold cavity with the slurry, the slurry may be preheated, for example, to about 52° C. (125° F.). Preheating the slurry to a temperature below the MGT reduces the viscosity of the slurry and allows the slurry to flow more easily. As stated above, the slurry may have been degassed in a vacuum. The slurry may be degassed again within the mold after the mold cavity is filled to remove air that may have been introduced during the filling of the mold cavity and to facilitate flow of the slurry into voids in the mold. Heat is applied to the mold having the cap 54 and the slurry, such as in an oven, until the slurry attains a temperature of about 150° C. As stated above, the slurry turns into gel at about 120° C., however, at about 150° C., the gel can bond to a polycarbonate cap 54. Depending on the material used to fabricate the cap 54, bonding may take place at temperatures other than about 150° C. If the cap 54 is fabricated of a material having a lower melting point than 120° C., then the gel pad 60, such as a gel slug 60, may be molded separately and then bonded to the cap. The slits 62, 64 may be molded into the gel pad 60 through the use of an insert in the form of the slit in the mold.

Once the temperature of the gel pad 60 reaches about 150° C., the gelcap 66 may be cooled, such as by air-cooling, cold-water immersion, or other cooling means that are well known in the art. At 150° C. the gel pad is soft and if it were distorted during cooling it would set with the distortion included. To reduce the likelihood of distorting the gel pad 60, the gelcap 66 may be cooled within the mold. Cooling times may vary based on parameters including size and configuration of the mold, quantity of gel, temperature and quantity of cooling medium, cooling medium properties and the mold material. As an example, the cooling time may be about two (2) hours if cooling in air and about fifteen (15) minutes if cooling in water. Whether cooling with air or water, the final properties of the gel are substantially the same. The gelcap 66 is typically cooled to about ambient room temperature, but may be cooled to lower temperatures. If the gelcap 66 is cooled to the freezing point of the gel, about 0° C., then the gel will freeze and become hard. This may be beneficial for other means of coupling the gel pad 60 to the cap 54, such as with a secondary operation. The gelcap 66 may be removed from the mold at any time after the gel has set.

When removed from the mold, the gel pad 60 typically has a tacky surface. The gelcap 66 may be coated with a powder, such as cornstarch, to substantially reduce or eliminate the tackiness of the cured gel pad 60.

As stated above, in another aspect, the gel pad 60 may be molded separately from the cap 54 and coupled to the cap 54 by a secondary operation, such as by bonding. In one aspect, the gel pad 60 may be molded into a gel slug 60 having an outer perimeter smaller than the inner cylindrical wall of the cap 54 and to a height higher that the height of the cap. Since the gel pad 60 is being molded separate from the cap 54, the slurry only needs to be heated until it reaches about 120° C. and completes the transformation from slurry into gel and the gel becomes substantially transparent. The gel slug 60 may then be placed within the inner cylindrical wall of the cap 54. The gel slug 60 may be cooled and/or frozen prior to placing it within the inner cylindrical wall of the cap 54. The gel slug 60 may be coupled to the cap 54 through compression molding with the gel slug being compressed longitudinally so that the outer perimeter of the gel slug expands and compresses against the inner cylindrical wall of the cap. The gel slug 60 and cap 54 are heated to a sufficient temperature for the polystyrene of the gel and the polymer of the cap to form bonds between the gel and the cap. Molding the gel slug 60 separately from the cap 54 and heat bonding the gel slug to the cap at a later time is especially useful when the cap is made of a material that has a lower melting temperature than the MGT. In such situations, the gel slug 60 can be molded first and heat bonded to the cap 54 without melting the cap.

Figure 21:
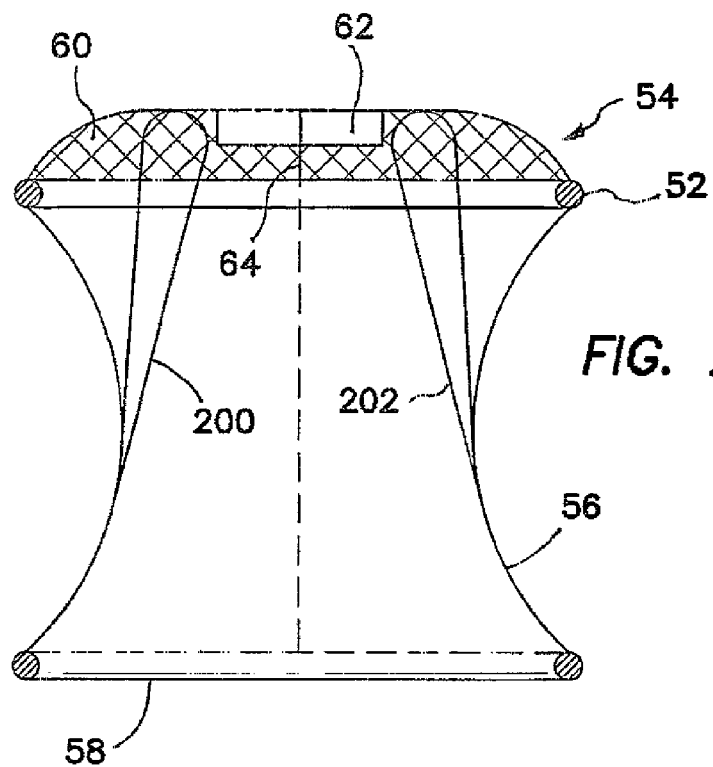
FIG. 21 depicts a side view of a hand access laparoscopic device having a gelcap, a retainer, a sleeve and a retention ring, with a plurality of stabilizers in the form of strings or tethers extending from the retention ring to the gelcap.
Figure 22:
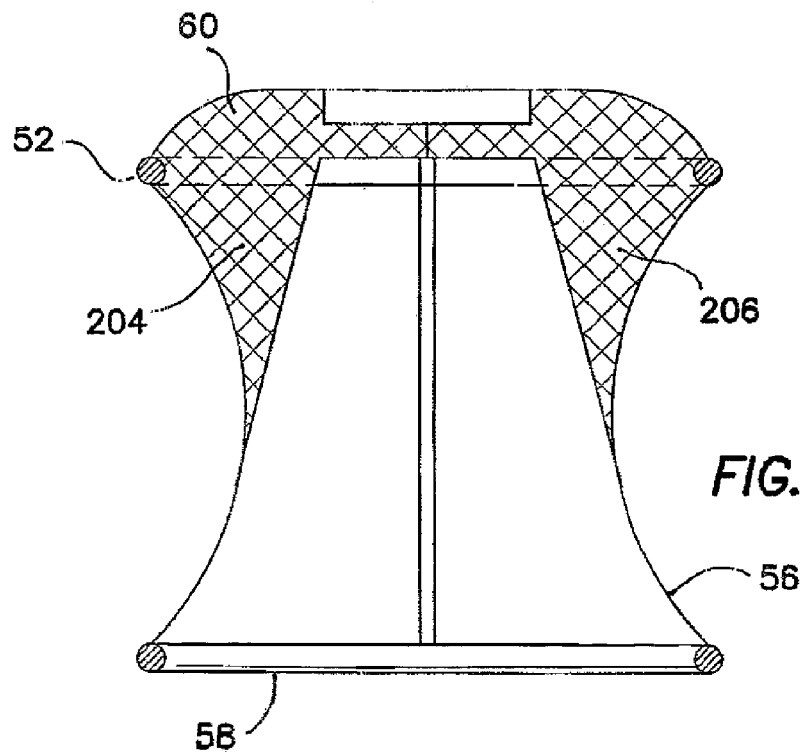
FIG. 22 depicts a side view of a hand access laparoscopic device having a gelcap, a retainer, a sleeve and a retention ring, with a plurality of stabilizers in the form of gussets or webs extending from the retention ring to the gelcap.

In reference to FIGS. 21-22, a cap 54 has the gel pad 60 attached, formed or integrated with the cap and is capable of being coupled to the retainer 52 which is capable of being coupled to the sleeve 56. In one aspect, the elongate sleeve 56 extends through an incision and is attached to a retention ring 58 that contacts the interior portions of the body cavity and provides tension between the retainer 52 outside the body cavity and the deformable retention ring. A plurality of stabilizers 200-206 extends from the retention ring 58 to the gel pad 60.

In one aspect, the stabilizers 200-206 are sized and configured to prevent excessive bulging of the gel pad 60 in response to the elevated body-cavity pressure. The stabilizers 200, 202, in one aspect, include a plurality of strings or tethers that extend from the retention ring 58 and subsequently through or into the gel pad 60. The stabilizers 204, 206 include a plurality of contiguous gel based gussets or webs that extend between the retention ring 58 and the gel pad 60

Figure 23:
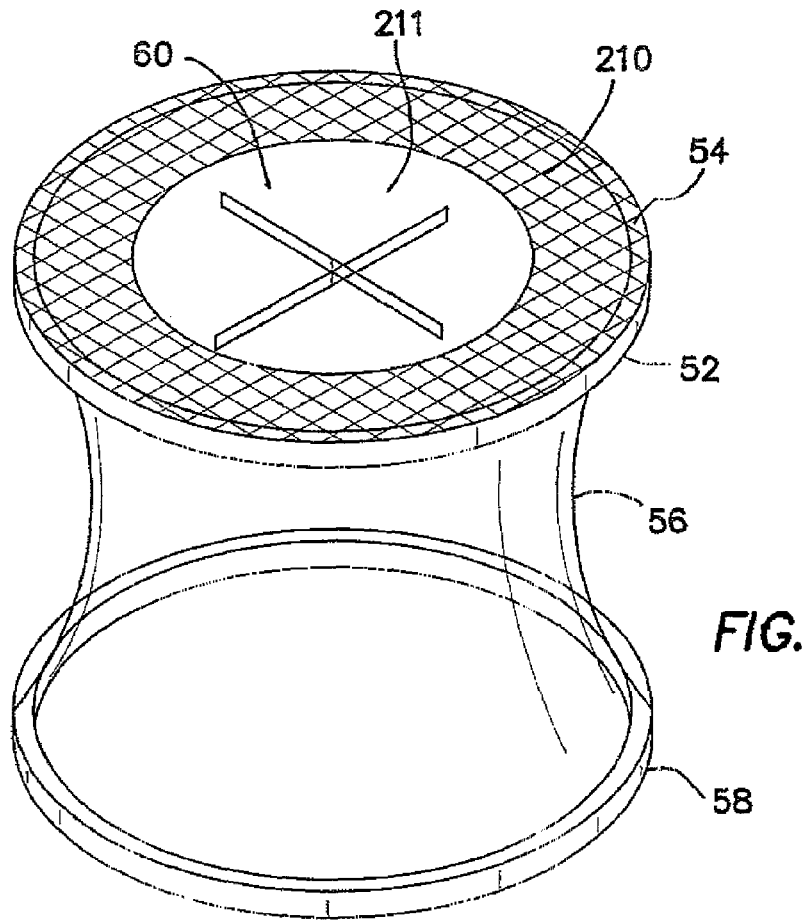
FIG. 23 depicts a top perspective view of a hand access laparoscopic device having a gelcap, a retainer, a sleeve and a retention ring, with a fabric integrated on the surface of the gel pad.
Figure 24:
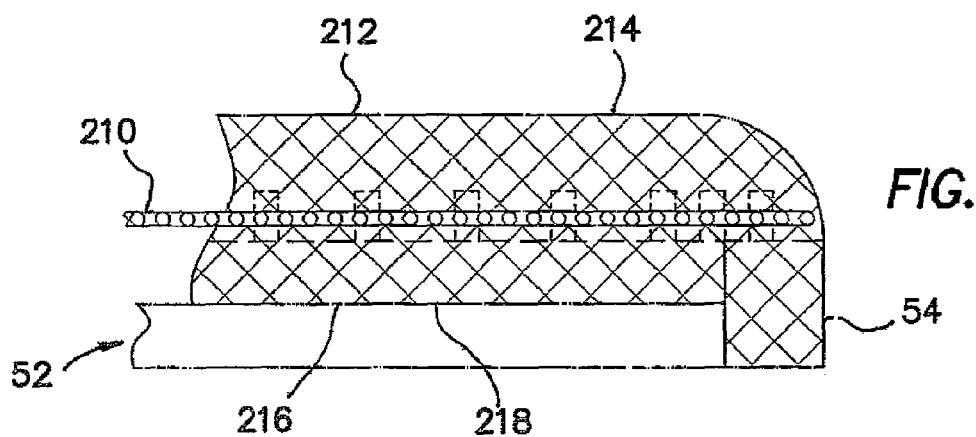
FIG. 24 depicts a partial side view of the hand access laparoscopic device of FIG. 23.

With reference to FIGS. 23-24, a cap 54 has a woven or knitted fabric 210 that is stretchable and/or resilient. The fabric 210 is integrated into or attached onto the surface 211 of the gel pad 60 and coupled to the periphery of the cap 54. The fabric 210 provides support to counteract the "doming" or "bowing" of the gel pad 60 or cap 54 under the influence of the internal inflation gas pressure associated with the inflation of the body cavity. In one aspect, a first fabric 212 can be integrated on a first surface 214 of the gel pad 60 and coupled to the periphery of the cap 54 and a second fabric 216 can be integrated on a second, opposite surface 218 and coupled to the cap. In this manner, counteracting support is provided in both directions to minimize uncontrolled deformation of the gel pad as a hand or instrument is placed through or withdrawn.

Figure 25:
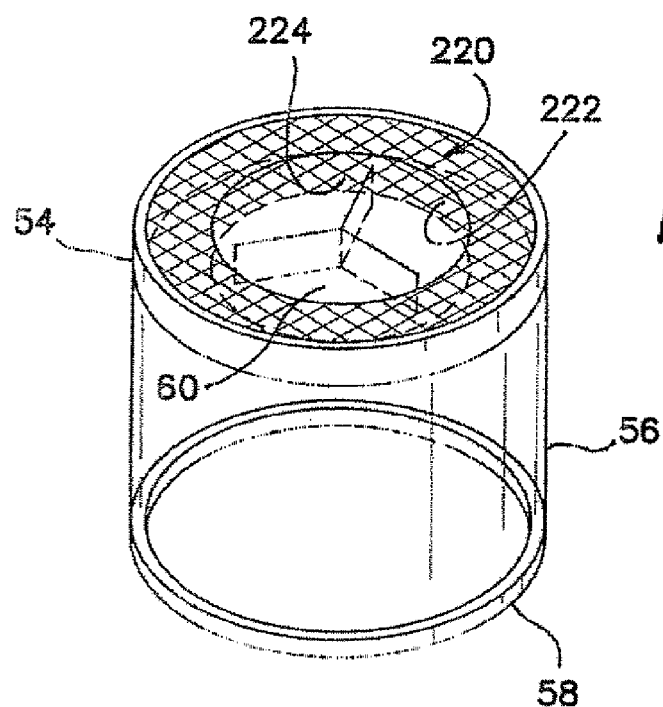
FIG. 25 depicts a top perspective view of a hand access laparoscopic device having a gelcap, a retainer, a sleeve and a retention ring, the gelcap having a cavity defined by fabric with the gel pad housed within the cavity.

In FIG. 25, a first fabric 220 is coupled to the periphery of the cap 54 and a second fabric 222 is coupled to the cap a distance from the first fabric. A cavity 224 is defined by the space between the first fabric 220 and the second fabric 222. The gel pad 60 may be inserted into the cavity 224 or otherwise held within the cavity. The gel pad 60 may be processed alone and formed to a preferred shape and size and firmness prior to coupling to the cap 54. The temperatures commonly required to process SEBS may substantially deform associated plastic structures. Therefore, separate processing and subsequent assembly may be useful for constructing a cap with the gel pad.

Figure 26:
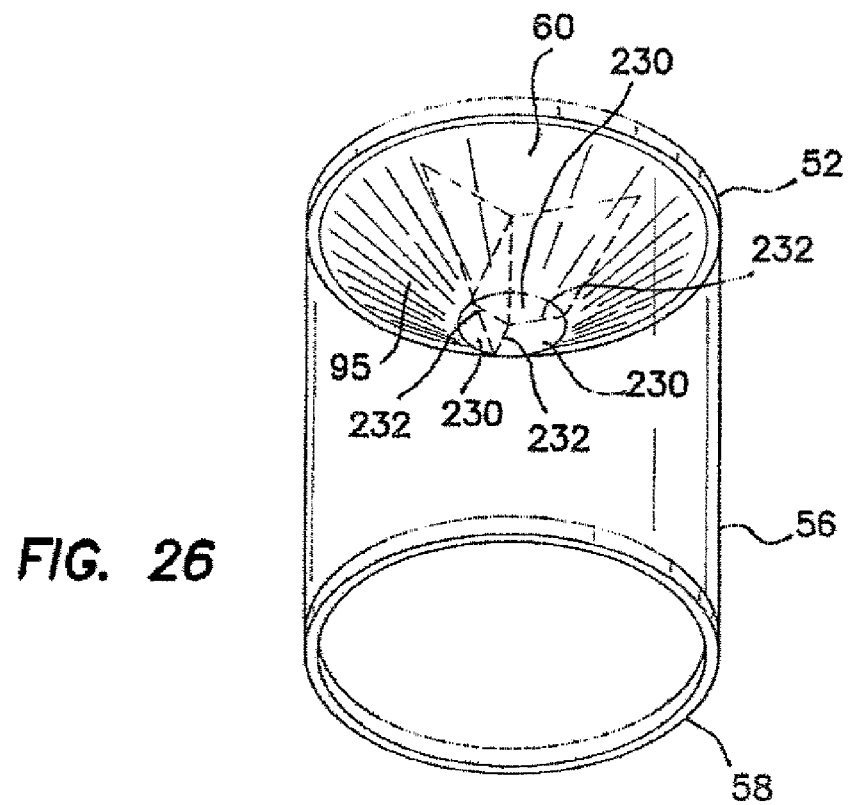
FIG. 26 depicts a bottom perspective view of a hand access laparoscopic device having a gelcap, a retainer, a sleeve and a retention ring, with the gel pad having multi-cusped lobes that seal upon one another.

Referring to FIG. 26, the gel pad 60 has multi-cusped lobes 230 that seal upon one another. The channel 232 through which a surgeon's hand or instruments may be inserted through is formed between individual lobes of the gel pad 60.

Accordingly, the present invention provides a hand access device and methods thereof. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive. The scope of the present invention is to be determined by the appended claims and their equivalents rather than the foregoing description.

What is claimed is:

1. A surgical access device comprising:
   a retractor comprising a proximal end; a distal end; a retention ring at the distal end of the retainer, wherein the retention ring is deformably insertable through an opening into a body cavity; and an elongate sleeve extending proximally from the retention ring;
   a gelcap couplable with the proximal end of the retractor, the gelcap comprising an annular cap ring defining a central opening; and a gel pad sealing the central opening and secured to the cap ring, wherein a periphery of the annular cap ring comprises a gap defining a first end of the cap ring and a second end of the cap ring;
   a latch pivotably coupled to the annular cap ring towards the first end of the cap ring;
   a latch receiver disposed on the cap ring towards the second end of the cap ring dimensioned to releasably receive the latch; and
   an access channel extending from a proximal end of the access device to a distal end of the access device, and through the gel pad and the cap ring of the gel pad, through the elongate sleeve, and through the retention ring,
   wherein
      in a first state in which the latch is not engaged with the latch receiver, the cap ring has a first diameter,
      in a second state in which the latch is engaged with the latch receiver, the cap ring has a second diameter smaller than the first diameter, and
      in the second state, the gel cap is coupled to the retractor.

2. The surgical access device of claim 1, wherein the latch comprises a shaft comprising a first end pivotably coupled to the first end of the cap ring, and a second end comprising an enlarged head.

3. The surgical access device of claim 2, wherein portions of the enlarged head are compressible.

4. The surgical access device of claim 1, wherein the latch comprises at least one projection that engages a corresponding notch in the latch receiver.

5. The surgical access device of claim 1, wherein the latch receiver comprises parallel walls defining a channel.

6. The surgical access device of claim 5, wherein the parallel walls flex away from each other when engaging the latch.

7. The surgical access device of claim 5, wherein the parallel walls comprises at least one projection that engages a corresponding notch in the latch.

8. The surgical access device of claim 1, wherein the cap ring comprises an inner, cylindrical wall.

9. The surgical access device of claim 1, wherein the gel pad is adhesively secured to the cap ring.

10. The surgical access device of claim 1, wherein the gel pad is mechanically secured to the cap ring.

11. The surgical access device of claim 10, wherein the cap ring comprises a wall comprising a plurality of apertures through which portions of the gel pad extend, mechanically securing the gel pad to the cap ring.

12. The surgical access device of claim 1, wherein the gel pad is solvent welded to the cap ring.

13. The surgical access device of claim 1, wherein the gel pad comprises an elastomeric gel.

14. The surgical access device of claim 13, wherein the elastomeric gel comprises a diblock or triblock copolymer, and mineral oil.

15. The surgical access device of claim 1, wherein the gel pad comprises an access portion comprising a plurality of dead-end slits through which the access channel extends.

16. The surgical access device of claim 1, wherein the cap ring comprises at least one of polymer, polyethylene, low density polyethylene, high density polyethylene, ultra high molecular weight polyethylene, and polycarbonate.

17. The surgical access device of claim 1, further comprising an annular retainer couplable to the proximal end of the elongate sleeve, positionable in the cap ring in the first state, and couplable to the cap ring in the second state.

* * * * *